(12) United States Patent
Tesse

(10) Patent No.: US 10,864,188 B2
(45) Date of Patent: *Dec. 15, 2020

(54) ANTI-MICROBIAL COMPOSITION

(71) Applicant: SEPTEOS, Paris (FR)

(72) Inventor: Nicolas Tesse, Vaucresson (FR)

(73) Assignee: SEPTEOS, Paris (FR)

( * ) Notice: Subject to any disclaimer, the term of this patent is extended or adjusted under 35 U.S.C. 154(b) by 10 days.

This patent is subject to a terminal disclaimer.

(21) Appl. No.: 15/269,364

(22) Filed: Sep. 19, 2016

(65) Prior Publication Data
US 2017/0000762 A1 Jan. 5, 2017

Related U.S. Application Data

(62) Division of application No. 13/992,387, filed as application No. PCT/EP2011/072390 on Dec. 9, 2011, now Pat. No. 9,474,723.

(60) Provisional application No. 61/421,315, filed on Dec. 9, 2010.

(30) Foreign Application Priority Data

Dec. 9, 2010 (EP) .................................... 10306385

(51) Int. Cl.
| | |
|---|---|
| A61K 31/045 | (2006.01) |
| A61K 31/11 | (2006.01) |
| A61K 31/222 | (2006.01) |
| A61P 31/04 | (2006.01) |
| A61P 1/04 | (2006.01) |
| A61K 31/352 | (2006.01) |
| A61K 9/00 | (2006.01) |
| A61K 31/04 | (2006.01) |
| A61K 31/08 | (2006.01) |
| A61K 31/22 | (2006.01) |
| A61K 31/37 | (2006.01) |
| A61K 45/06 | (2006.01) |
| A61K 47/10 | (2017.01) |
| A61K 47/32 | (2006.01) |
| A01N 65/24 | (2009.01) |
| A61K 36/54 | (2006.01) |
| A01N 35/02 | (2006.01) |
| A61K 31/015 | (2006.01) |
| A61K 31/235 | (2006.01) |
| A61K 31/35 | (2006.01) |

(52) U.S. Cl.
CPC ............ *A61K 31/352* (2013.01); *A01N 35/02* (2013.01); *A01N 65/24* (2013.01); *A61K 9/0014* (2013.01); *A61K 9/0019* (2013.01); *A61K 31/015* (2013.01); *A61K 31/04* (2013.01); *A61K 31/045* (2013.01); *A61K 31/08* (2013.01); *A61K 31/11* (2013.01); *A61K 31/22* (2013.01); *A61K 31/222* (2013.01); *A61K 31/235* (2013.01); *A61K 31/35* (2013.01); *A61K 31/37* (2013.01); *A61K 36/54* (2013.01); *A61K 45/06* (2013.01); *A61K 47/10* (2013.01); *A61K 47/32* (2013.01); *A61P 1/04* (2018.01); *A61P 31/04* (2018.01); *Y02A 50/30* (2018.01)

(58) Field of Classification Search
CPC ........ A01N 35/02; A01N 65/24; A61K 31/11; A61K 36/54; A61K 31/045; A61K 31/222; A61P 1/04; A61P 31/04
See application file for complete search history.

(56) References Cited

U.S. PATENT DOCUMENTS

| 4,477,361 | A | 10/1984 | Sperti et al. | |
|---|---|---|---|---|
| 9,474,723 | B2 * | 10/2016 | Tesse | ................... A61K 9/0014 |
| 2003/0003140 | A1 | 1/2003 | Domb et al. | |
| 2007/0292540 | A1 * | 12/2007 | Gow | ...................... A61K 36/54 |
| | | | | 424/739 |
| 2012/0077875 | A1 | 3/2012 | Tesse | |

FOREIGN PATENT DOCUMENTS

| FR | 2946255 A1 | 12/2010 |
|---|---|---|
| WO | WO 2006/080013 A2 | 8/2006 |
| WO | WO 2010/139805 A1 | 12/2010 |

OTHER PUBLICATIONS

Mayaud et al. (Letters in Applied Microbiology, 2008, 47, 167-173).*
James et al. (Gastrointestinal Infections, Oct. 18, 2009, http://www.aboutkidshealth.ca/En/ResourceCentres/PregnancyBabies/Babies/HealthIssuesinYourBaby/Pages/Gastrointestinal-Infections.aspx).*
Senthilingann, CNN, Mar. 28, 2018, https://www.cnn.com/2018/03/28/health/uk-man-multidrug-resistant-gonorrhea-intl/index.html). (Year: 2018).*
Ali et al., "Chemical Composition and Antimicrobial Activities of the Essential Oils of Cinnamomum aureofulvum Gamb.", J. Essential Oil Research, vol. 14, No. 2, Mar./Apr. 2002, pp. 135-138, XP009125688.
Chang et al., "Antibacterial activity of leaf essential oils and their constituents from Cinnamomum osmophloeum," Journal of Ethnopharmacology, vol. 77, No. 1, 2001, pp. 123-127, XP027380307.

(Continued)

*Primary Examiner* — Theodore R. West

(74) *Attorney, Agent, or Firm* — Birch, Stewart, Kolasch & Birch, LLP

(57) ABSTRACT

This invention pertains to an anti-microbial, in particular anti-bacterial and/or anti-fungal composition comprising cinnamaldehyde, trans-2-methoxycinnamaldehyde, cinnamyl acetate and linalool. In particular this composition is intended for preventing and/or treating microbial infection in an animal.

6 Claims, 3 Drawing Sheets

(56) References Cited

OTHER PUBLICATIONS

Cheng et al., "Chemical polymorphism and antifungal activity of essential oils from leaves of different provenances of indigenous cinnamon (*Cinnamomum osmophloeum*)," Bioresource Technology, vol. 97, No. 2, 2006 (Available online Apr. 13, 2005), pp. 306-312, XP025106072.

Communiqué 2006, "Comite de L'Antibiogramme de La Societe Francaise de Microbiologie," Edition of Jan. 2006, pp. 14-16 (4 pages total).

Dugoua et al. "From type 2 diabetes to antioxidant activity: a systematic review of the safety and efficacy of common and cassia cinnamon bark," Canadian Journal of Physiology and Pharmacology, vol. 85, No. 9, 2007 (Published on NRC Research Press Web site Oct. 5, 2007), pp. 837-847, XP009149536.

Ezzaouia et al., "Investigation of essential oils to fight multiresistant bacteria in hygienic and therapeutic applications," International Journal of Essential Oil Therapeutics, Jan. 2007, vol. 1, No. 2, pp. 51-55, XP009096945.

Liang et al., "Antibacterial and antioxidant properties of Ramulus Cinnamomi using supercritical $CO_2$ extraction," European Food Research and Technology, 2008 (Published online Mar. 14, 2008), vol. 227, No. 5, pp. 1387-1396, XP019621812.

Ooi et al., "Antimicrobial Activities of Cinnamon Oil and Cinnamaldehyde from the Chinese Medicinal Herb *Cinnamomum cassia* Blume," The American Journal of Chinese Medicine, vol. 34, No. 5, 2006, pp. 511-522, XP009125629.

Quale et al., "In Vitro Activity of Cinnamomum zeylanicum Against Azole Resistant and Sensitive *Candida* Species and a Pilot Study of Cinnamon for Oral Candidiasis," American Journal of Chinese Medicine, vol. XXIV, No. 2, 1996, pp. 103-109, XP009117732.

Randrianarivelo et al., "Composition and antimicrobial activity of essential oils of Cinnamosma fragrans," Food Chemistry, vol. 114, No. 2, 2009, pp. 680-684, XP025924758.

Rattanachaikunsopon et al., "Potential of cinnamon (*Cinnamomum verum*) oil to control *Streptococcus iniae* infection in tilapia (*Oreochromis niloticus*)," Fisheries Science, vol. 76, No. 2, 2010 (Published online Feb. 10, 2010), pp. 287-293, XP002593860.

Shahverdi et al., "Trans-Cinnamaldehyde from Cinnamomum zeylanicum Bark Essential Oil Reduces the Clindamycin Resistance of Clostridium difficile in Vitro," Journal of Food Science, vol. 72, No. 1, 2007, pp. S55-S58, XP002472467.

Unlu et al., "Composition, antimicrobial activity and in vitro cytotoxicity of essential oil from Cinnamomum zeylanicum Blume (*Lauraceae*)," Food and Chemical Toxicology, vol. 48, No. 11, 2010, pp. 3274-3280.

Ojagh et al., "Development and evaluation of a novel biodegradable film made from chitosan and cinnamon essential oil with low affinity toward water," Food Chemistry, vol. 122, Issue 1, Sep. 2010 (Available online Feb. 16, 2010), pp. 161-166.

\* cited by examiner

ANTI-MICROBIAL COMPOSITION

CROSS REFERENCE TO RELATED APPLICATIONS

This application is a Divisional of copending application Ser. No. 13/992,387, filed on Jun. 7, 2013, which was filed as PCT International Application No. PCT/EP2011/072390 on Dec. 9, 2011, which claims the benefit under 35 U.S.C. § 119(e) to U.S. Provisional Application No. 61/421,315, filed on Dec. 9, 2010, and under 35 U.S.C. § 119(a) to patent application Ser. No. 10/306,385.5, filed in Europe on Dec. 9, 2010, all of which are hereby expressly incorporated by reference into the present application.

This invention pertains to an anti-microbial, in particular anti-bacterial, more particularly against Gram − bacteria, and/or anti-fungal and/or anti-viral composition comprising cinnamaldehyde, trans-2-methoxycinnamaldehyde, cinnamyl acetate and linalool. In particular this composition is intended for preventing and/or treating microbial infection in an animal.

The arrival of penicillin followed by streptomycin in the 40s opened the era of anti-bacterials. The discovery of anti-bacterial compounds such as penicillin, aminosides, macrolides and quinolones have been one of the biggest achievement of the modern medicine for the treatment of bacterial infections.

However, there is a growing need for new compounds or compositions allowing fighting bacterial infections. This need is in particular due to the fact that there is more and more microbes which are exhibiting various drug resistance to known anti-microbial compounds or compositions.

For example in the case of bacteria it becomes a major problem to find novel efficient anti-bacterial compositions to prevent or treat bacterial infections. For example among Gram + bacteria exhibiting drug resistance can be cited *Staphylococcus*, in particular *Staphylococcus aureus*, *Enterococcus*, in particular *Enterococcus faecalis* and *Enterococcus cloaceae*, and *Propionibacter*, in particular *Propionibacter acnes*, and among Gram − bacteria exhibiting drug resistance can be cited *Escherichia*, in particular *Escherichia coli*, *Pseudomonas*, in particular *Pseudomonas aeruginosa*, and *Acinetobacter*, in particular *Acinetobacter baumanii*, *Serratia*, in particular *Serratia marscescens*, *Citrobacter*, in particular *Citrobacter freundii*, *Klebsiella*, in particular *Klebsiella pneumonia*, and *Enterobacter*, in particular *Enterobacter aerogenes*.

A particularly significant case is *Staphylococcus aureus* for which more than 95% of the *Staphylococcus aureus* strains are penicillin resistant and more than 60% are also resistant to its methicilline derivative (MRSA). Moreover some strains are resistant to vancomycin (VRSA).

According to WHO, the ratio of methicillin-resistant *Staphylococcus aureus* strains which became mipiromicin (an anti-bacterial inhibiting protein synthesis) resistant increased from 2.7% to 65% in three years time. This shows that the action of classical anti-bacterial analogs may be quickly countered by multiple resistance mechanisms from bacteria.

This drug resistance is even more preoccupying as at present it is not confined to hospital but is also disseminated outside. For example, there is a very important prevalence of infections of person over 65 years old caused by *Staphylococcus aureus*. Thus, the proportion of microbial infections, in particular bacterial, pneumonia, endocarditis, osteoarticular or urinary infections, developed by persons over 65 years old and linked with *Staphylococcus aureus* is particularly preoccupying.

Gram negative bacteria, in particular enterobacteria and *Pseudomonas aeruginosa*, are naturally resistant to, often at low level of, most hydrophobic and/or high molecular weight anti-microbial agents, for example such as penicillin G, penicillin M, macrolides, rifampicin, fusidic acid, novobiocine, vancomycine, as this anti-microbials cannot cross the external membrane wall of the bacteria.

Apparition and propagation of microbial strains resistant to almost all or even to all the known anti-microbial agents becomes a major health issue.

There is clearly a growing need for novel anti-microbial, in particular anti-fungal and/or anti-bacterial compounds, in particular to fight with Gram + and/or Gram − bacteria.

Thus, one aim of the invention is to provide active anti-microbial agents, in particular anti-fungal and/or antibacterial, more particularly having a large spectra and/or efficient with resistant microbes, even more particularly to non-natural resistant and/or to natural resistant microbes.

The "natural resistance" may be as defined pages 15, 16 and 17 of the Communiqué 2006 (Edition of January 2006) of the "Comité de l'Antibiogramme de la Société Française de Microbiologie".

In infectious pathology, a bacteria is said «resistant» when it may bear a concentration much higher than the concentration which is possible to reach in vivo by a treatment.

Thus, another aim of the invention is to obtain antimicrobial agents exhibiting a high activity, in particular at low level, on their targets.

Known anti-microbial agents may exhibit the following drawbacks they may have an insufficient activity, in particular at low level and/or when interfering agent are present, they may be insufficiently active or not active at all on some or on any drug resistant microbes, in particular on drug resistant bacteria such as drug resistant *Staphylococcus aureus*, for example such as MRSA, VRSA; drug resistant *enterobacter*, such as NDM-1, or New Dehli Metallo-beta-lactamase type 1; they may presenting undesirable side effects, they may not be well tolerated by the organism, their use may lead to bacteria having drug resistance, in particular crossed drug resistance, they may be expensive, and/or difficult to obtain.

More particularly cinnamon essential oils, especially those comprising trans-cinnamaldehyde, or trans-cinnamaldehyde alone are known to be a potent anti-microbial, however, they lead to undesirable effects, such as neurotoxicity, which may lead to death in case of high dose, hepatotoxicity, irritation of the skin, sensitization of the skin, phototoxicity and/or photoallergy.

Thus, the invention aims to composition solving all or part of these problems. In particular the invention aims to anti-microbial agents exhibiting high activity, in particular at low level and/or when interfering agent are present, activity on some or as many as possible microbes, in particular drug resistant microbes, in particular activity on:
  bacteria, for example drug resistant bacteria such as drug resistant *Staphylococcus aureus*, for example such as MRSA, VRSA, drug resistant *enterobacter*, such as NDM-1; and at least one bacteria such as those disclosed below;
  fungi, for example
    Epidermal, dermal and/or keratinous appendage fungi, in particular *Candida, Trichophyton, Malassezia,* and *Microsporum,*

Systemic, in particular non-opportunistic disease, more particularly due to *Blastomyces, Coccidioides*, and opportunistic disease due to *Aspergillus, Candida albicans*, and *Cryptococcus*, viruses, such as HIV; herpes viruses, the hepatitis B and C viruses, and influenza A and B viruses, in particular enveloped viruses presenting as few as possible side effects well tolerated by the organism; leading to as few as possible or not leading at all to drug resistance, in particular to cross drug resistance; reproducible; obtained through a process easy to follow analytically, for example with HPLC and/or GC; cheap; and/or easy to obtain.

Definitions

An "anti-microbial" is a substance that kills or inhibits the growth of microorganisms such as bacteria, fungi, or viruses. Antimicrobial drugs either kill microbes (microbiocidal) or prevent the growth of microbes (microbiostatic). Disinfectants and antiseptics are antimicrobial substances used on non-living objects or outside the body.

By «anti-bacterial active», is meant a compound or a composition exhibiting bacteriostatic or bactericidal properties, in particular in vitro, for example in a composition such as a pharmaceutical composition, a food composition or a cosmetic composition, or for disinfecting industrial plants or livestock farming, or in vivo, more particularly with animals or human beings.

Antibiotics are a class of medication used specifically for treating bacterial infections by helping the organism to fight the bacterial infection.

By «resistant bacteria», is meant a bacteria resistant or less sensitive than usually expected to at least one classic antibiotic and/or anti-bacterial drug, while this bacteria belongs to a species which should be sensitive or a priori sensitive. The classic antibiotic and/or anti-bacterial drug may be chosen from the compounds belonging to families listed below By «multi-resistant bacteria» is meant, a bacteria resistant to several antibiotic(s) and/or anti-bacterial(s), in particular for which the species should be sensitive or a priori sensitive, "non-natural drug resistance", more particularly a bacteria presenting at least two non-natural drug resistance. More particularly, the expression "multi-resistant" may apply to a bacterium or a stock of bacteria resistant to all antibiotics tested in at least two antibiotic classes.

Antiviral drugs are a class of medication used specifically for treating viral infections. Like antibiotics, viruses may evolve to resist the antiviral drug.

By "anti-fungal" is meant a compound or a composition exhibiting fungistatic or fungicidal properties, in particular in vitro, for example in a composition such as a pharmaceutical composition, a food composition or a cosmetic composition, or for disinfecting industrial plants or livestock farming, or in vivo, more particularly with animals or human beings.

An anti-fungal may be active on moulds, yeast and/or dimorphic fungi, in particular on a subject, such as an animal, and in particular a human being.

A substance or a composition is bacteriostatic/virustatic/fungistatic when the bacteria/virus/fungi multiplication is suspended or stopped. Experimentally the Minimum Inhibitory Concentration (MIC) is the lowest concentration of the substance or composition where no bacterial/viral/fungical growth is observed after 18 to 24 h of contact in favourable conditions to bacterial/viral/fungal growth.

A substance or a composition is bactericidal/virucidal/fungicidal when it definitively destroys the vitality of bacteria/virus/fungi. Experimentally, the logarithmic fall of bacteria/virus/fungi population is measured. The batericidal/virucidal/fungicidal effect is defined as a fall of 3 Log of the bacteria/virus/fungi population. The "bactericidal effect" may also be defined as in example 5.

By «nosocomial infection» is meant all microbial infections resulting from treatment in an hospital or a healthcare service unit, in particular with the apparition of symptoms happening at least 25 h, more particularly at least 48 h, after the subject is admitted in the hospital or within 30 days after discharge.

A genotoxic product is a product that shows an effect on the genetic material of a cell. The genotoxicity may be measured by Ames test, in particular according to ICH guidelines. A carcinogen product is a product that shows an effect on the genetic material of a cell, this effect is transmissible through mitosis and may leads to apparition of tumours, in particular measured in compliance with the OECD guideline 474.

"Not carcinogen" and/or "non genotoxic" means that at the dosage at which this the composition is used, no carcinogenic and/or no genotoxic effect is shown By "Interfering agents" is meant organic or mineral compounds which in contact to the anti-microbial agent reduces or avoids the anti-microbial effects. By example, it is well-known that alcohol or iodine are inactivated by proteins (in particular albumin) and minerals. As examples of interfering agents, one can notably cite bovine albumine and/or sheep erythrocytes.

By "the composition is free of X" is meant that the amount of X is lower than 10 ppm by weight compared to the total weight of the composition, in particular lower than 1 ppm by weight compared to the total weight of the composition, and more particularly lower than 0.1 ppm by weight compared to the total weight of the composition, and even lower than 0.01 ppm by weight compared to the total weight of the composition, more particularly its means that 0 ppm of X is present in the composition.

The «synergy» is be calculated as follows:

$$FIC_{index}=(MIC_{A/B}/MIC_A)+(MIC_{B/A}/MIC_B)$$

where $FIC_{index}$ is the index of the Fractional Inhibitory Concentration, $MIC_A$=MIC of the A compound alone, $MIC_B$=MIC of the B compound alone, $MIC_{A/B}$=MIC of the A compound, in the mixture A+B, MIC $B_A$=MIC of the B compound, in the mixture A+B.

This formula allows determining the effect, as when:

$FIC_{index}$ is less or equal to 0.5 there is a synergic effect, $FIC_{index}$ is more than 0.5 and less or equal to 1 there is an additive effect, $FIC_{index}$ is more than 1 and less or equal to 4 an indifferent effect, and $FIC_{index}$ is more than 4 there is an antagonistic effect.

By "excipient" is meant all compounds which do not belong to active blend and which is not anti-microbial activity or which is used for other reasons than its potential anti-microbial activity.

Figure 1:
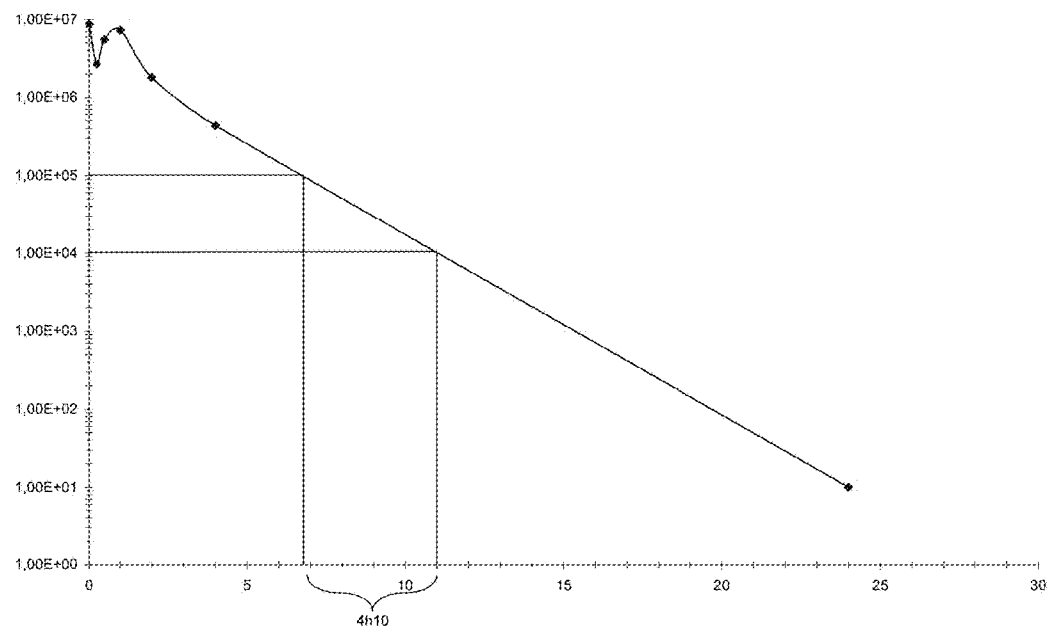
FIG. 1 CFU/ml versus time (h)
Figure 2:
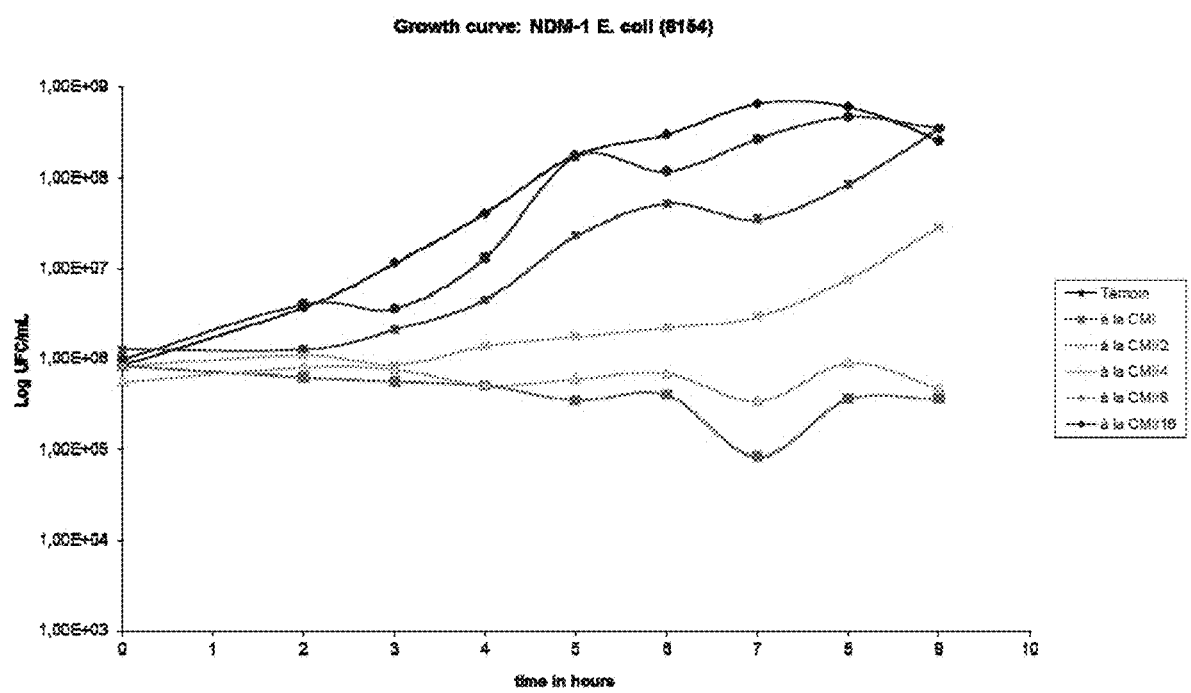
FIG. 2 Growth curves of NDM-1 *E. coli* in the presence of increasing concentrations of active blend 1
Figure 3:
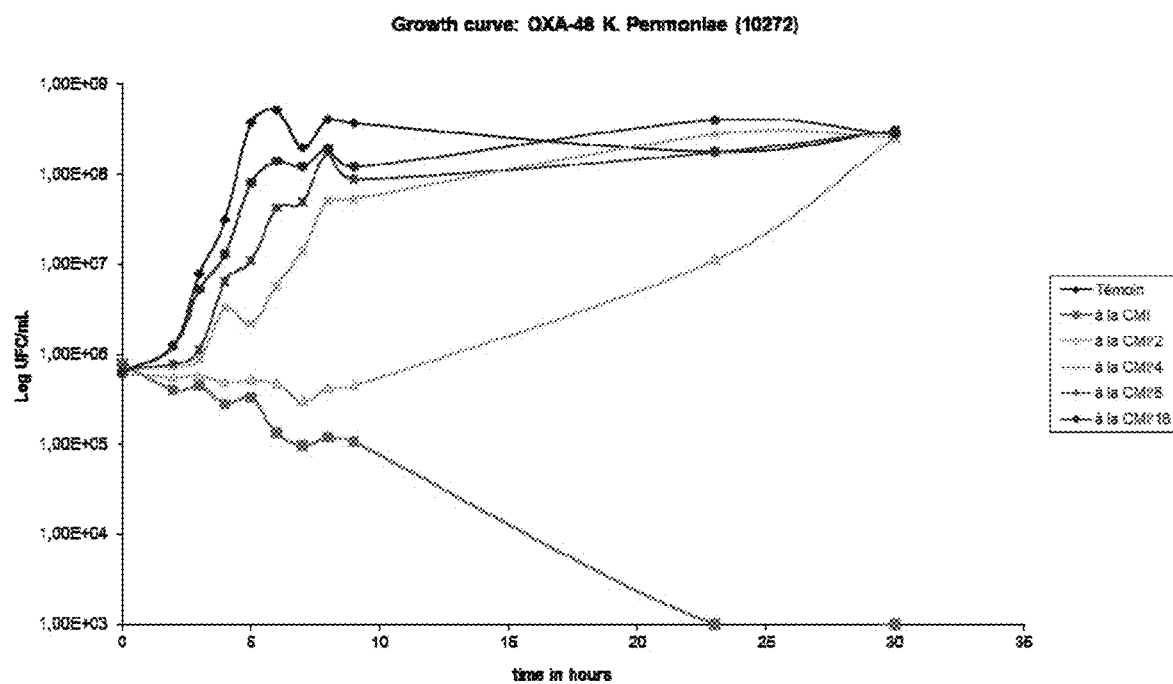
FIG. 3 Growth curves of OXA-48 *K. pneumoniae* in the presence of increasing concentrations of active blend 1
Figure 4:
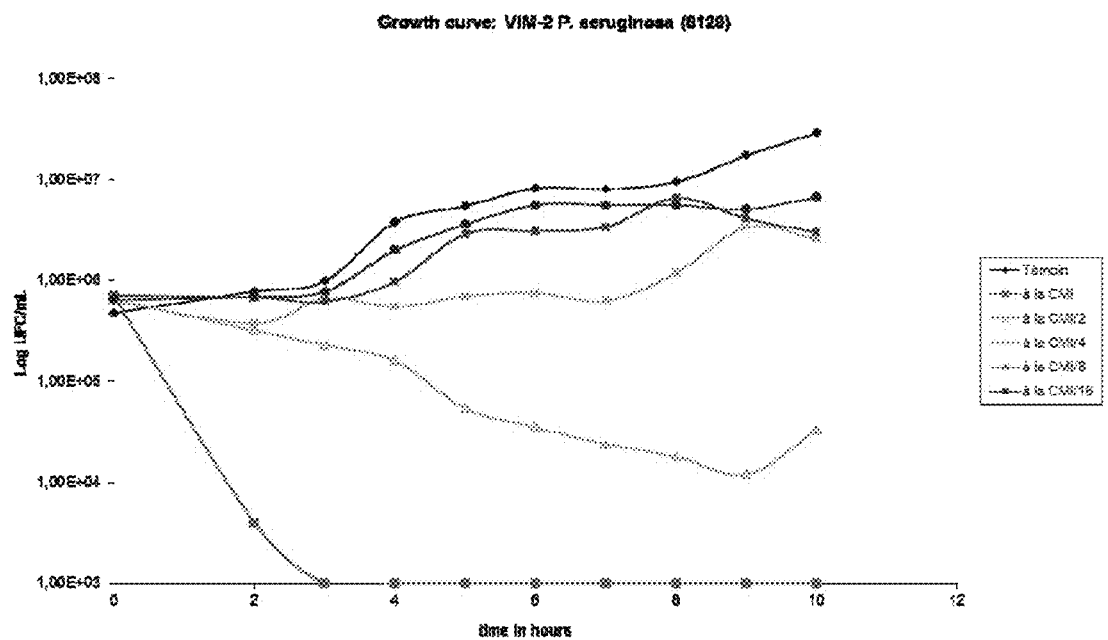
FIG. 4 Growth curves of VIM-2 *P. aeruginosa* in the presence of increasing concentrations of active blend 1
Figure 5:
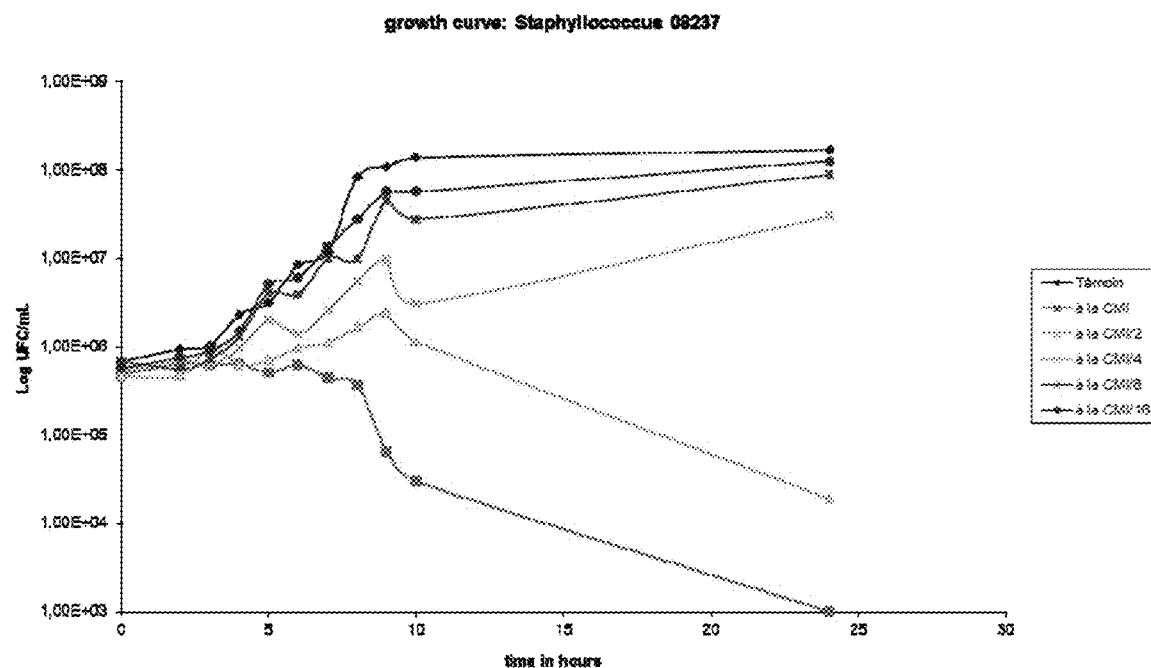
FIG. 5 Growth curves of Staphyllococcus strain 8237
Figure 6:
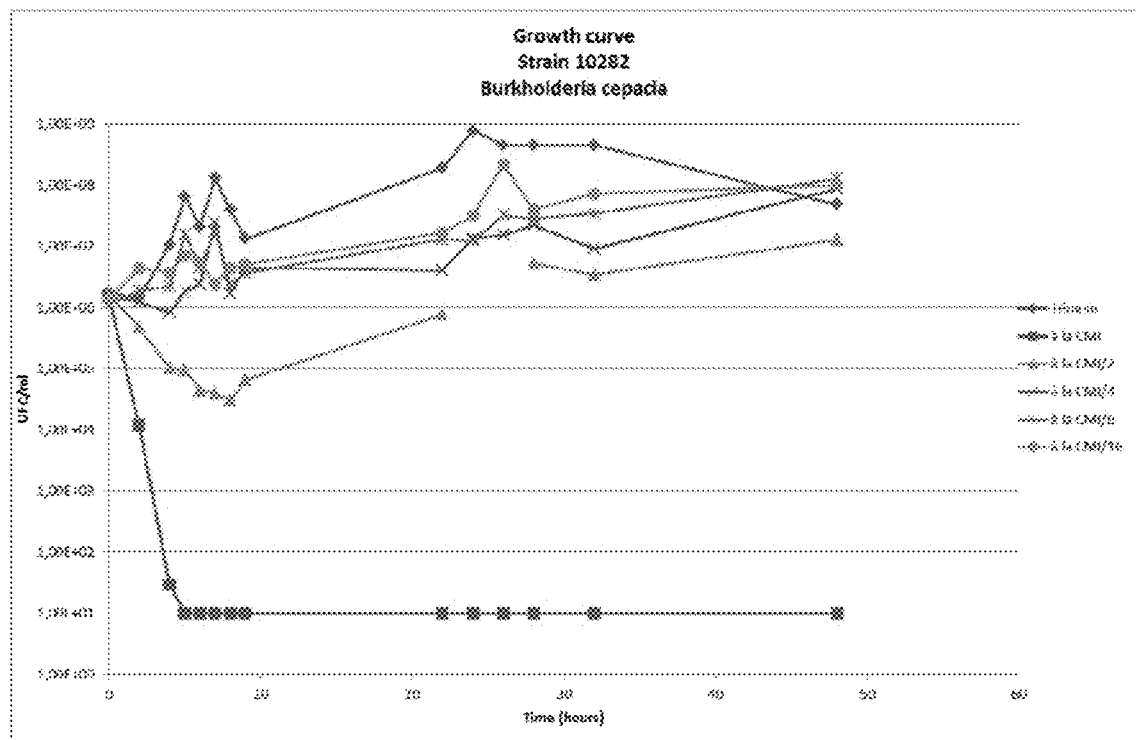
FIG. 6 Growth curves of strain 10282 Burkhloderia cepacia

For the growth curve, the following symbols are used:

| ♦ control | × CMI/4 |
|---|---|
| ■ CMI | * CMI/8 |
| ▲ CMI/2 | • CMI/16 |

DISCLOSURE OF THE INVENTION

Following a first aspect, the invention has for subject matter a composition, in particular a pharmaceutical composition, comprising:
  a synergistic active blend comprising, or consisting of:
    trans-cinnamaldehyde, trans-2-methoxycinnamaldehyde, cinnamyl acetate, and linalool,
  optionally cineole, beta-caryophyllene and/or benzyl benzoate,
  optionally a drug, in particular an antibiotic or an antiviral drug,
  optionally a carrier, in particular a pharmaceutically acceptable carrier,
and wherein the total amount of coumarin and/or safrole is below 1% by weight compared to the total weight of the composition, more particularly the total amount of coumarin and/or safrole is below 1% by weight, in particular below 0.5% by weight, and more particularly is below 0.1% by weight compared to the total weight of active blend.

The composition is preferably a synthetic one which consequently is chemically well defined and shows reproducible properties, what is essential in the pharmaceutical field. In addition, the composition is not carcinogen and preferably further non genotoxic. To this end, the composition preferably comprises amounts of coumarin and/or safrole lower than 1% by weight compared to the total weight of the composition, even more particularly the composition is free of coumarin and/or safrole, still more particularly free of coumarin and safrole.

In a preferred embodiment, coumarin content is less than 0.5% by weight, particularly less than 0.1% by weight, more particularly less than 0.01% by weight compared to the total weight of the composition.

In a preferred embodiment, safrole content is less than 0.5% by weight, particularly less than 0.1% by weight, more particularly less than 0.01% by weight compared to the total weight of the composition.

The composition may comprise eugenol in an amount of less than 0.5% by weight, more particularly of less than 0.1% by weight, more particularly less than 0.01% by weight compared to the total weight of the composition. Following an embodiment, the composition is free of eugenol.

The composition is preferably free of coumarin, safrole and eugenol.

This low amount of coumarin, safrole and/or eugenol, or even the absence of coumarin, safrole and/or eugenol, may lead to a composition exhibiting low or no carcigenocity and/or genotoxicity, more particularly no carcigenocity. In particular the composition shows no carcinogenic effect and optionally very little, or even no, genotoxic effect, more particularly compared to trans-cinnamaldehyde.

Trans-cinnamaldehyde may comprise an amount of cis-cinnamaldehyde of less than 50% by weight, in particular less than 20% by weight, more particularly less than 10% by weight, in particular less than 5% by weight, even less than 2% by weight, very particularly less than 1% by weight. Following an embodiment, trans-cinnamaldehyde is free of cis-cinnamaldehyde. The definition of trans-cinamaldehyde also encompasses its ester (in particular methylic and ethylic ester derivatives) derivatives as well as pharmaceutical acceptable salts thereof. CNM is sometimes used as abbreviation of trans-cinnamaldehyde.

Trans-2-methoxycinnamaldehyde may comprise an amount of cis-2-methoxy cinnamaldehyde of less than 20% by weight, in particular less than 10% by weight, more particularly less than 5% by weight, even less than 2% by weight, very particularly less than 1% by weight. Following an embodiment, trans-2-methoxycinnamaldehyde is free of cis-2-methoxycinnamaldehyde.

The trans-cinnamaldehyde may range from 70 to 95% by weight, in particular from 75 to 92% by weight, and more particularly from 80 to 90% by weight compared to the total weight of the active blend. According to an embodiment, the amount of trans-cinnamaldehyde ranges from 85 to 90% by weight, and more particularly is around 86.7% by weight compared to the total weight of the active blend.

The trans-2-methoxycinnamaldehyde may range from 2 to 10% by weight, in particular from 3 to 9% by weight, and more particularly from 3.5 to 7.5% by weight compared to the total weight of the active blend. According to an embodiment, the amount of trans-2-methoxycinnamaldehyde ranges from 4.5 to 7% by weight, and more particularly is around 5.35% by weight compared to the total weight of the active blend.

The cinnamyl acetate may range from 1.0 to 7.5% by weight, in particular from 1.5 to 6% by weight, and more particularly from 1.75 to 5% by weight compared to the total weight of the active blend. According to an embodiment, the amount of cinnamyl acetate ranges from 2 to 5% by weight, and more particularly is around 2.5% by weight compared to the total weight of the active blend.

The linalool may range from 0.5 to 7% by weight, in particular from 1 to 6% by weight, and more particularly from 1.5 to 5% by weight compared to the total weight of the active blend. According to an embodiment, the amount of linalool ranges from 1.5 to 4% by weight compared to the total weight of the active blend, and more particularly is around 2.4% by weight compared to the total weight of the active blend.

The beta-caryophyllene may range from 0.2 to 5% by weight, in particular from 0.5 to 4% by weight, and more particularly from 0.8 to 3.5% by weight compared to the total weight of the active blend. According to an embodiment, the amount of beta-caryophyllene ranges from 1 to 2.5% by weight compared to the total weight of the active blend, and more particularly is around 1.7% by weight compared to the total weight of the active blend.

The cineole may range from 0.1 to 4% by weight, in particular from 0.2 to 3.5% by weight, and more particularly from 0.3 to 2.5% by weight compared to the total weight of the active blend. According to an embodiment, the amount of cineole ranges from 0.5 to 2.0% by weight compared to the total weight of the active blend, and more particularly is around 1.0% by weight compared to the total weight of the active blend.

The benzyl benzoate may range from 0.02 to 3% by weight, in particular from 0.05 to 1.5% by weight, and more particularly from 0.1 to 1% by weight compared to the total weight of the active blend. According to an embodiment, the amount of cineole ranges from 0.15 to 0.75% by weight compared to the total weight of the active blend, and more particularly is around 0.35% by weight compared to the total weight of the active blend.

In an embodiment, the active blend comprises, or consists of, trans-cinnamaldehyde, trans-2-methoxycinnamaldehyde, cinnamyl acetate and linalool, in particular each component ranges in the amount disclosed above.

In an embodiment, the active blend comprises, or consists of, trans-cinnamaldehyde, trans-2-methoxycinnamaldehyde, cinnamyl acetate, linalool and cineole, in particular each component ranges in the amount disclosed above. In a variant, cinnamyl acetate ranges from 1.5 to 7.5% by weight, in particular from 2 to 6% by weight, more particularly from 2.5 to 5% by weight, and more particularly around 2.5% by weight compared to the total weight of the active blend.

In an embodiment, the active blend comprises, or consists of, trans-cinnamaldehyde, trans-2-methoxycinnamaldehyde, cinnamyl acetate, linalol and beta-caryophyllene, in particular each component ranges in the amount disclosed above.

In an embodiment, the active blend comprises, or consists of, trans-cinnamaldehyde, trans-2-methoxycinnamaldehyde, cinnamyl acetate, linalol and benzyl benzoate, in particular each component ranges in the amount disclosed above.

In an embodiment, the active blend comprises, or consists of, trans-cinnamaldehyde, trans-2-methoxycinnamaldehyde, cinnamyl acetate, linalol, cineole and beta-caryophyllene, in particular each component ranges in the amount disclosed above. In a variant, cinnamyl acetate ranges from 1.5 to 7.5% by weight, in particular from 2 to 6% by weight, more particularly from 2.5 to 5% by weight, and more particularly around 2.5% by weight compared to the total weight of the active blend.

In an embodiment, the active blend comprises, or consists of, trans-cinnamaldehyde, trans-2-methoxycinnamaldehyde, cinnamyl acetate, linalol, cineole and benzyl benzoate, in particular each component ranges in the amount disclosed above.

In an embodiment, the active blend comprises, or consists of, trans-cinnamaldehyde, trans-2-methoxycinnamaldehyde, cinnamyl acetate, linalol, beta-caryophyllene and benzyl benzoate, in particular each component ranges in the amount disclosed above.

In a specific embodiment, the active blend comprises, or consists of, trans-cinnamaldehyde, trans-2-methoxycinnamaldehyde, cinnamyl acetate, linalol, cineole, beta-caryophyllene, and benzyl benzoate, in particular each component ranges in the amount disclosed above. This active blend is the preferred active blend.

Following a specific embodiment, the active blend comprises, or consists of:
around 1% by weight of cineole compared to the total weight of the active blend,
around 2.4% by weight of linalool compared to the total weight of the active blend,
around 1.7% by weight of beta-caryophyllene compared to the total weight of the active blend,
around 86.7% by weight of trans-cinnamaldehyde compared to the total weight of the active blend,
around 5.35% by weight of trans-2-methoxycinnamaldehyde compared to the total weight of the active blend,
around 0.35% by weight of benzyl benzoate compared to the total weight of the active blend, and
around 2.5% by weight of cinnamyl acetate compared to the total weight of the active blend,
in particular free of coumarin and/or safrole, even more particularly free of coumarin and safrole.

By "around X %" may be meant plus or minus 10%, for example around 5% means in the range of 4.5 to 5.5%.

It has been surprisingly discovered that the active blend shows synergistic effects with the consequence that the antimicrobial effect (namely not only the antibacterial effect but also the antiviral or the antifungal effect) of the active blend is better than the antimicrobial effect of trans-cinnamaldehyde. As a consequence, the effective amount of trans-cinnamaldehyde in the composition, in particular in a drug, can be lowered resulting in a composition, in particular a drug, with reduced toxicity and preferably improved efficacy.

In addition, it has been surprisingly discovered that the active blend, in comparison to trans-cinnamaldehyde alone or to cinnamon essential oils (especially *Cinnamomum cassia* or *Cinnamomum zeylanicum* or their mixtures), has a broad spectrum of activity, also on Gram – bacteria.

In particular, the composition of the invention shows activity on most of possible microbes, including drug resistant microbes, in particular activity on:
bacteria, for example drug resistant bacteria such as drug resistant *Staphylococcus aureus*, for example such as MRSA, VRSA, drug resistant *enterobacter*, such as NDM-1; and at least one bacteria such as those disclosed below;
fungi, for example
Epidermal, dermal and/or keratinous appendage fungi, in particular *Candida, Trichophyton, Malassezia*, and *Microsporum,*
Systemic, in particular non-opportunistic disease, more particularly due to *Blastomyces, Coccidioides*, and opportunistic disease due to *Aspergillus, Candida albicans*, and *Cryptococcus,*
viruses, such as HIV; herpes viruses, the hepatitis B and C viruses, and influenza A and B viruses, in particular enveloped viruses.

The composition of the invention is consequently a wide spectrum antibacterial and/or antifungal and/or antiviral drug.

The anti-microbial effect of the composition is also observed for anaerobic bacteria.

The anti-microbial effect of the composition is effective even at low content in trans-cinnamaldehyde and/or when interfering agent are present.

Moreover, in comparison to trans-cinnamaldehyde alone, the MIC and/or the kinetics of the activity of the active blend is increased at least to one or more bacteria as defined below. In particular, it has been discovered that the active blend of the invention is able to decrease bacterial division at sub-MIC concentrations while trans-cinnamaldehyde is not.

In addition, it has been surprisingly discovered that the composition of the invention reduces the log reduction time in comparison to trans-cinnamaldehyde alone, meaning in particular that the composition of the invention acts more quickly and/or shows a bactericidal/virucidal/fungicidal effect.

Furthermore, it has been surprisingly discovered that the active blend shows very good properties regarding to the low induction, which may be around zero or which is zero, of drug resistance to microbes, in particular bacteria. This active blend may have a very low level of crossed resistance induction.

The active blend may also not induce, or to a very low level, the apparition of mutant bacteria (resistant strains).

The active blend has very good efficiency as anti-microbial, in particular as anti-bacterial, and/or anti-fungal, and/or anti-viral, more particularly as anti-bacterial.

The composition of the invention further shows very interesting results on viruses, in particular on enveloped viruses. It is believed by the inventors that the composition of the invention may act on membranes of the bacteria/viruses/fungi.

The active blend may be present in an amount ranging from 0.1 to 100% by weight compared to the total weight of the composition.

In one embodiment the amount of active blend ranges from 0.1 to 20% by weight, in particular from 0.2 to 10% by weight, more particularly from 0.3 to 5% by weight, and even more particularly from 0.5 to 2.5% by weight compared to the total weight of the composition. In this case the composition may be intended for an external use or for topical use or for treating surfaces.

In another embodiment the amount of active blend ranges from 0.1 to 100%, in particular from 0.1 to 70% or from 10 to 100% by weight, in particular from 15 to 95% by weight, more particularly from 25 to 80% by weight, and even more particularly from 50 to 75% by weight compared to the total weight of the composition. In this case the composition may be intended for an internal use or systemic use.

Following an embodiment, the composition, in particular the pharmaceutical composition further comprises at least one, and in particular one, antibiotic.

The antibiotics which may be used in the present invention, in particular in the pharmaceutical composition, more particularly for use for preventing and/or treating bacterial infection(s), are numerous and may be gathered by families according to their spectrum of action, of their chemical structure, like according to their mode of action on the bacteria.

According to a particular mode of realization, the antibiotic or at least one of the antibiotic is selected among:
1. antibiotics acting on the bacterial wall, in particular, interfering with the synthesis of peptidoglycane,
2. antibiotics operating the membranes of the cells, external membrane and/or cytoplasmic membrane,
3. antibiotics acting on the synthesis of proteins, in particular on bacterial ribosome,
4. antibiotics blocking the synthesis of messenger RNA,
5. antibiotics acting on DNA, for example cut of the bits of DNA and unfolding of the DNA or inhibition of the replication of DNA,
6. antibiotics acting by competitive inhibition, in particular an antibiotic interfering with the folate metabolism,
7. one of their pharmaceutically acceptable salts, and
8. one of their combinations.

As example, the antibiotics acting on the bacterial wall can be selected among (A) the fosfomycin (or phosphomycin), (B) an antibiotic of the family of the glycopeptides, such as the vancomycin, the teicoplanin (or teichoplanin), the ristocetin, or the avoparcin, or (C) an antibiotic of the family of the beta-lactam antibiotics.

The family of beta lactamins is in particular represented by (A) the penams, in particular the group G of penicillin G, the group M of antistaphylococcic penicillins, the group has amino-benzylpenicillin (ampicillin), the group of acyl-ureido-penicillins, the group of the amidino-penicillins and the group of the inhibitors of the betalactamases, (B) the penems and the carbapenems, such as the meropenem (or meropenem) and the imipenem, (C) the cephems, in particular the cephalosporins of $1^{st}$, $2^{nd}$ and $3^{rd}$ generation, and (D) the monobactams.

The beta-lactam antibiotics have as targets of proteins present on the external face of the membrane cytoplasmic and called proteins binding penicillin (PLP).

As example, the antibiotics operating the membranes of the cells can be selected among the family of the polymyxins, the family of the gramicidines, and the tyrocidin. Still as example, the antibiotics acting on bacterial ribosome, can be selected among the fusidic acid, the family of the aminosides, the family of phenicoles, the family of the tetracyclins, the family of the oxazolidinones and groups it macrolides, lincosamides and synergistins (or streptogramins).

As for antibiotics blocking the synthesis of messenger RNA, they include in particular the family of the rifamycins, represented by the rifamycin SV and the rifampicin. The rifamycins are fixed on under unit B of RNA polymerase and prevent the initiation of the synthesis of mRNA.

Always as example the antibiotics acting on DNA can be selected among the family of the quinolones, the family of the fluoroquinolones, and the products nitrated such as the nitro-imidazoles oxyquinoleins, nitrofurans or nitro-imidazoles.

Lastly, the antibiotics interfering with the metabolism of the folates include the family of sulphamides and the trimethoprim.

According to a particular mode of realization, the antibiotic or at least one of the aforesaid antibiotic is selected among the meropenem, the rifampicin and the tigecyclin.

According to a particular mode of realization, the antibiotic or one of the aforesaid antibiotic is the meropenem or the rifampicin.

More particularly, the antibiotic may be chosen from the following:
aminosides,
betalactamins, as betalactamins cephalosporins, betalactamins penicillins, and other betalactamins (carbapenems, monobactame),
cyclins, such as doxycyclin, limecyclin, metacyclin, minocyclin, tetracyclin, oxtetracyclin, tigecyclin,
glycopeptides, such as teicoplanin and vancomycin, and polypeptides,
macrolides and macrolides like, such as lincosamides, ketolides and synergistins,
quinolones, in particular fluoroquinolones,
anti-bacterial peptides, such as gramicidin,
phages, and
others, such as fusidic acid, noxytiolin, daptomycin, fosfomycin, oxazolidinone, phenicoles, polymyxins, rifampicin, . . . .

It has been surprisingly discovered that the active blend of the invention is able to potentiate the antibiotics, advantageously meaning that the effect and/or the scope of the antibiotic is increased. Furthermore, the combination active blend of the invention plus antibiotic can be efficient against bacteria which are resistant to the antibiotic of the combination. Thus, the active blend of the invention can be used to re-sensibilize bacteria towards antibiotic It has been surprisingly discovered that the antibiotics is able to potentiate the active blend of the invention, advantageously meaning that the effect and/or the scope of the active blend of the invention is increased.

The synergy effect is particularly observed with antibiotics with other target than the membrane (gentamicin, amikacin, erythromycin and clindamycin).

The composition, in particular the pharmaceutical composition, preferably comprises the antibiotic(s) at its normal doses or at a reduced dosis (in comparison to the normal doses known by the skilled person).

Following an embodiment, the composition, in particular the pharmaceutical composition, further comprises at least one, and in particular one, antiviral drug.

The antiviral drug can in particular chosen from: entry inhibitors, fusion inhibitors, Integrase inhibitor, Interferon type III, Interferon type II, Interferon type I, Interferon, Nucleoside analogues, Protease inhibitor, Reverse transcriptase inhibitor, Synergistic enhancer (antiretroviral), In particular, the antiviral drug can in particular chosen from: Abacavir, Aciclovir, Adefovir, Amantadine, Amprenavir, Rintatolimod, Atazanavir, Emtricitabine/tenofovir/efavirenz, Boceprevir, Darunavir, Delavirdine, Didanosine, Docosanol, Edoxudine, Efavirenz, Emtricitabine, Enfuvirtide, Entecavir, Famciclovir, Fomivirsen, Fosamprenavir, Foscarnet, Ganciclovir, Ibacitabine, combinatinon of inosine, acetamidobenzoic acid, and dimethylaminoisopropanol, Idoxuridine, Imiquimod, Indinavir, Inosine, Lamivudine, Lopinavir, Loviride, Maraviroc, Moroxydine, Methisazone, Nelfinavir, Nevirapine, Oseltamivir, Peginterferon alfa-2a, Penciclovir, Peramivir, Pleconaril, Podophyllotoxin, Raltegravir, Ribavirin, Rimantadine, Ritonavir, Pyramidine, Saquinavir, Stavudine, Tea tree oil, Tenofovir, Tenofovir disoproxil, Tipranavir, Trifluridine, Trizivir, Tromantadine, Truvada, Valaciclovir (Valtrex), Valganciclovir, Vicriviroc, Vidarabine, Viramidine, Zalcitabine, Zanamivir (Relenza), Zidovudine, The composition, in particular the pharmaceutical composition, preferably comprises the antiviral drug(s) at its normal doses or at a reduced dosis (in comparison to the normal doses known by the skilled person The composition, in particular the pharmaceutical composition, may comprise a carrier. The carrier may range from 0.1 to 99.9% by weight, preferably from 0.5 to 99.9% by weight, more preferably from 1 to 99.5% by weight, more preferably from 1 to 80% by weight, compared to the total weight of the composition.

In particular, the carrier is such that it allows to analytically follow the process to obtain the composition, in particular the pharmaceutical composition, for example with HPLC and/or GC analysis, more particularly capillary analysis.

In an embodiment, the carrier comprises or consists of, less than ten excipients, more particularly less than eight, even more particularly less than five excipients, more particularly less than four excipients, still more particularly less then three excipients, and even more particularly one excipient.

Thus the composition, in particular the pharmaceutical composition, may consist of:
the active blend, in particular consisting of trans-cinnamaldehyde, trans-2-methoxycinnamaldehyde, cinnamyl acetate, and linalool, and optionally cineole, beta-caryophyllene, and/or benzyl benzoate,
optionally at least one, in particular one, antibiotic and/or antiviral drug, and
optionally a carrier consisting of less than ten excipients, more particularly less than eight, even more particularly less than five excipients.

When the excipient is a compound bearing at least a charge "one excipient" may mean one compound under different salt forms.

Following one embodiment, the carrier represents 95 to 99.9% by weight compared to the total weight of the composition, in particular the remaining is the active blend, more particularly the composition is intended for an external use, for example meaning external to the skin or to the mucosa of the subject.

Following another embodiment, the carrier represent 0.5 to 50% by weight compared to the total weight of the composition, in particular the remaining is the active blend, more particularly the composition is intended for an internal use.

The carrier may be solid, liquid, gel, or pasty.

The carrier may comprise, or consists of, one or more excipient, in particular pharmaceutically acceptable, and optionally one or more additive such as preservatives, vitamins, minerals.

Following a specific embodiment, the composition, in particular the pharmaceutical composition, comprises, or consists of:
an active blend comprising, or consisting of:
trans-cinnamaldehyde ranging from 70 to 95% by weight, in particular from 75 to 92% by weight, more particularly from 80 to 90% by weight, even more particularly from 85 to 90% by weight, and more particularly around 86.7% by weight compared to the total weight of the active blend,
trans-2-methoxycinnamaldehyde ranging from 2 to 10% by weight, in particular from 3 to 9% by weight, more particularly from 3.5 to 7.5% by weight, even more particularly from 4.5 to 7% by weight, and more particularly around 5.35% by weight compared to the total weight of the active blend,
cinnamyl acetate ranging from 1 to 7.5% by weight, in particular from 1.5 to 6% by weight, more particularly from 1.75 to 5% by weight even more particularly from 2 to 5% by weight, and more particularly around 2.5% by weight compared to the total weight of the active blend,
linalool ranging 0.5 to 7% by weight, in particular from 1 to 6% by weight, more particularly from 1.5 to 5% by weight, even more particularly from 1.5 to 4% by weight, and more particularly around 2.4% by weight compared to the total weight of the active blend,
cineole ranging from 0.1 to 4% by weight, in particular from 0.2 to 3.5% by weight, more particularly from 0.3 to 2.5% by weight, even more particularly from 0.5 to 2.0% by weight, and more particularly around 1.0% by weight compared to the total weight of the active blend,
beta-caryophyllene ranging from 0.2 to 5% by weight, in particular from 0.5 to 4% by weight, more particularly from 0.8 to 3.5% by weight, even more particularly from 1 to 2.5% by weight, and more particularly is around 1.7% by weight compared to the total weight of the active blend, and
benzyl benzoate ranging from 0.02 to 3% by weight, in particular from 0.05 to 1.5% by weight, more particularly from 0.1 to 1% by weight, even more particularly from 0.15 to 0.75% by weight, and more particularly is around 0.35% by weight compared to the total weight of the active blend,
a carrier ranging from 0 to 99.9% by weight, in particular from 0.1 to 90% by weight, more particularly from 1 to 80% by weight compared to the total weight of the composition,
and wherein the composition is free of coumarin and/or safrole, and optionally is free of eugenol.

The composition may be intended for a use as an antimicrobial composition, such as anti-bacterial and/or anti-fungal and/or anti-viral composition. It may thus be used as a cleaning agent, in particular to clean medical devices which are intended to be in contact with the skin or mucosa, and more particularly when potential breaches may exist. For example this composition may be used on skin surface where an infusion is to be done or on skin or mucosa surface where a catheter is used, in particular urinary catheter.

The composition may also be used as a conservative, in particular for food or cosmetic composition.

The composition may also be used for cleaning and/or protecting a surface from a secondary colonisation.

The invention is more particularly directed to a pharmaceutical composition.

Following one embodiment, the pharmaceutical composition is free of classic antibiotics or antiviral drugs, in particular as disclosed in the description.

Following another embodiment, the pharmaceutical composition comprises at least one classic antibiotic and/or antiviral drug, in particular as disclosed in the description.

In particular, the pharmaceutical composition is for use in anti-microbial, such as anti-bacterial and/or anti-fungal and/or anti-viral, prevention and/or treatment of a subject, advantageously even in the presence of interfering agents.

A subject may be an animal such as production animals, for example cattle, swine and poultry, pets, for example dog or cat, or a human being.

Following an embodiment, the pharmaceutical composition is for use as anti-bacterial prevention and/or treatment of a subject, in particular in the case of a drug-resistant fungi and/or bacteria, more particularly to antibiotics, even more particularly to one or several of the classic antibiotics disclosed in this description.

The pharmaceutical composition may have a microbicidal activity, in particular a bactericidal activity, more particularly when interfering substance(s) is(are) present, such as bovine albumine and/or sheep erythrocytes.

The bacteria may be aerobic or anaerobic. Interestingly, the medicament of the invention shows a wide spectrum of activity on all kind of bacteria, including Gram − bacteria, which can further be resistant or multi-resistant.

Following a specific embodiment, the active blend and/or the composition, in particular as pharmaceutical composition or as a conservative, is bactericidal.

As was said before, more and more bacteria become drug resistant to one or several of these anti-bacterial agents, in particular to antibiotics, more particularly to classic antibiotics, for example such as those listed in the description.

Principal actual anti-bacterial agents are more active on, or even are specific of, Gram + or Gram − bacteria. More particularly, most of the known anti-bacterial are active on, or even are specific of, Gram + bacteria. There is thus a need for anti-bacterial compositions, in particular pharmaceutical compositions, able to stop the development or to destroy the vitality of Gram − bacteria, and advantageously also of Gram + bacteria.

In particular, the compositions, more particularly the pharmaceutical compositions, according to the invention, present an activity toward Gram − and Gram + bacteria. They can be efficient toward non drug resistant and/or drug resistant bacteria, in particular toward multi-resistant bacteria.

In particular, the compositions, more particularly pharmaceutical compositions, are active toward drug-resistant Gram − bacteria strains such as:

*Pseudomonas*, and more particularly *P. aeruginosa*;
*Acinetobacter*, and more particularly *A. baumanii*;
*Escherichia*, and more particularly *E. coli*;
*Enterobacter* and more particularly *E. aerogenes* and/or *E. cloacae*;
*Serratia*, in particular *Serratia marscescens*;
*Citrobacter*, in particular *Citrobacter freundii*; and/or
*Klebsiella*, in particular *Klebsiella pneumonia*.

It has also been shown that the compositions, more particularly pharmaceutical compositions, may be active toward drug-resistant Gram + bacteria strains such as:

*Staphylococcus*, in particular *S. aureus*;
*Enterococcus*, in particular *E. faecalis*; and/or
*Propionibacter*, in particular *Propionibacter acnes*.

Compositions, more particularly pharmaceutical compositions, may be active toward anaerobic bacteria, in particular:

*Bacteroides*, such as *B. fragilis* and *B. thetaiotaomicron*;
*Eggerthella*, such as *E. lenta*;
*Peptostreptococcus*, such as *P. micros*, *P.* spp, and *P. anaerobius*;
*Clostridium*, such as *C. perfringens* and *C. difficile*; and/or
*Micromonas*.

In a first embodiment the bacteria is of the group *Pseudomonas*, in particular drug-resistant *Pseudomonas*, more particularly at least one drug resistance, even more particularly two, three, four, five or six drug resistance chosen among:

fluoroquinolones resistance;
cephalosporins resistance in particular 1st, $2^{nd}$ or $3^{rd}$ generation;
production of a penicillinase, meaning betalactamins penicillins resistance, in particular in case of hyperproduction of chromosomic cephalosporinase;
production of extended spectrum betalactamase (ESBL, ex: types PER-1 or GES-2);
production of a metallo-betalactamase, in particular of VIM-2 type;
lack of porin, in particular D2 porin, which may lead to betalactamins other than penicillins and cephalosporins resistance; and
aminosides resistance.

In a second embodiment the bacteria is of the group *Acinetobacter*, in particular drug-resistant *Acinetobacter*, more particularly at least one drug resistance, even more particularly two, chosen among:

multiresistance;
Vietnamese expanded Spectrum betalactamase VEB-1; and
production of a metallo-betalactamase, in particular of VIM-4 type.

In a third embodiment the bacteria is of the group *Escherichia*, in particular drug-resistant *Escherichia*, more particularly at least one drug resistance, even more particularly two, chosen among:

fluoroquinolones and quinolones resistance;
cephalosporins resistance in particular 1st, $2^{nd}$ or $3^{rd}$ generation;
production of extended spectrum betalactamase (ESBL);
production of a metallo-betalactamase, ex: NDM-1 type;
production of a carbapenemase, ex KPC-2 type; and
production of a penicillinase.

In a fourth embodiment the bacteria is of the group *Staphyloccocus*, in particular drug-resistant *Staphyloccocus*, more particularly at least one drug resistance, even more particularly two, chosen among:

methicillin resistance;

aminosides resistance; in particular tobramycin/kanamycin resistance: KT phenotype; and fluoroquinolones resistance.

In a fifth embodiment the bacteria is of the group *Enteroccocus*, in particular drug-resistant *Enteroccocus*, more particularly at least one drug resistance, even more particularly two, chosen among:

aminosides resistance; and macrolides and apparented macrolides resistance.

In a sixth embodiment the bacteria is of the group *Enterobacter*, in particular drug-resistant *Enterobacter*, more particularly at least one drug resistance, more particularly production of extended spectrum betalactamase resistance (ESBL).

production of extended spectrum betalactamase (ESBL, ex: types PER-1 or GES-2); and production of a carbapenemase, ex KPC-2 type.

In a seventh embodiment the bacteria is of the group *Propionibacter*, in particular drug-resistant *Propionibacter*, more particularly at least one drug resistance, even more particularly two.

In an eighth embodiment the bacteria is of the group *Serratia*, in particular drug-resistant *Serratia*, more particularly at least one drug resistance, even more particularly two, chosen among:

production of a carbapenemase, ex KPC-2 type; and production of extended spectrum betalactamase (ESBL, ex: types SME-1 or SME-2);

In an ninth embodiment the bacteria is of the group *Citrobacter*, in particular drug-resistant *Citrobacter*, more particularly by production of a carbapenemase, ex KPC-2 type.

In an tenth embodiment the bacteria is of the group *Klebsiella*, in particular drug-resistant *Klebsiella*, more particularly at least one drug resistance, even more particularly two, chosen among:

production of a carbapenemase, ex KPC-2 type or VIM; and production of extended spectrum betalactamase (ESBL, ex: type OXA 48).

According to another embodiment, the composition may be active toward bacteria from $1^{st}$, $2^{nd}$, $3^{rd}$, $4^{th}$, $5^{th}$, $6^{th}$, $7^{th}$, $8^{th}$, $9^{th}$, $10^{th}$ embodiments and their mixture, for example mixture of 2, 3, 4, 5, 6, 7, 8, 9 and even the 10 embodiments.

The composition may be active, bacteriostatic and/or bactericidal, on Gram − and/or Gram + bacteria, in particular to drug resistant bacteria, and more particularly to at least 1, 2, 3, 4, 5, 6, 7, 8, 9, 10 or 11, in particular to 1, 2, 3, 4, 5, 6, 7, 8, 9, 10 or 11, bacteria chosen from:

Gram − bacteria, for example such as:

*Pseudomonas*, for example *Pseudomonas aeruginosa*, in particular drug resistant, more particularly VIM-2, GES-2 or PER-1;

*Acinetobacter*, for example *Acinetobacter baumanii*, in particular drug resistant, more particularly VIM-4;

*Escherichia*, for example *Escherichia coli*, in particular drug resistant, more particularly NDM-1 or KPC-2;

*Enterobacter*, for example *Enterobacter aerogenes*, in particular drug resistant;

*Serratia*, for example *Serratia marscescens*, in particular drug resistant, more particularly KPC-2, SME-2 or SME-1;

*Citrobacter*, for example *Citrobacter freundii*, in particular drug resistant, more particularly KPC-2; and

*Klebsiella*, for example *Klebsiella pneumonia*, in particular drug resistant, more particularly KPC-2;

and/or to Gram + bacteria, for example such as:

*Staphylococcus*, for example *Staphylococcus aureus*, in particular drug resistant;

*Enterococcus*, for example *Enterococcus faecalis* and *Enterococcus cloacae*, in particular drug resistant, more particularly *Enterococcus cloacae* GES-5, KPC-2; and/or

*Propionibacter*, for example *Propionibacter acnes*, in particular drug resistant.

The composition may be active, fungistatic or fungicidal, to fungi, in particular to drug resistant fungi, and more particularly to at least 1, 2, 3, 4, 5, 6, 7, 8, 9, 10 or 11 fungi chosen from:

Epidermal, dermal and/or keratinous appendage fungi, in particular *Candida*, *Trichophyton*, *Malassezia*, and *Microsporum*, Systemic, in particular non-opportunistic disease, more particularly due to *Blastomyces*, *Coccidioides*, and opportunistic disease due to *Aspergillus*, *Candida albicans*, and *Cryptococcus*.

The composition may be active towards viruses, in particular HIV, herpes viruses, the hepatitis B and C viruses, and influenza A and B viruses. The composition is particularly active on non-encapsulated viruses. The composition is particularly active on enveloped viruses.

The pharmaceutical composition may be for use for anti-microbial prevention and/or treatment of a subject, for example for preventing and/or treating a disease and/or an infection caused by one or several, in particular two or three, bacteria such as the ones disclosed in the description, more particularly drug resistant and/or multiresistant bacteria; and/or fungus, and/or viruses. Following an embodiment the bacteria is an anaerobic bacteria.

The infections may be chosen from urinary system infection, respiratory system infection, digestive system infection, central nervous system infection, skin and soft tissues infection, bone infection, articulations infection, muscles infection, vasculary system infection, diabetic foot and eschar.

The pharmaceutical composition may thus be used for prevention and/or treatment of syndromes or diseases, in particular induced by a microbial infection, in particular such as bacterial and/or fungus and/or viruses infection, more particularly by bacteria and/or fungus and/or viruses disclosed in the instant description, wherein the syndrome and/or disease may concern:

gastroenterology sphere, in particular syndromes and/or disease linked to digestive tube, more particularly Crohn disease (specifically in view of the good results obtained on anaerobic bacteria) and peptic ulcer, dermatology, in particular syndromes and/or disease linked to skin, more particularly diabetic foot and eschars, systemic infections which can be treated via systemic administration diseases linked to infections of urinary system, diseases linked to infections of respiratory system, diseases linked to infections of digestion system, diseases linked to infections of central nervous system, diseases linked to infections of skin and soft tissues, diseases linked to infections of bones, articulations an muscles, diseases linked to infections of vascular system, and/or septic shock,

AIDS

Herpes

Hepatitis B and C.

More particularly, the pharmaceutical composition is for use for preventing or treating, in particular treating, infections, in particular bacterial infections, leading to bacteremia, Crohn disease, peptic ulcer, diabetic foot and/or eschars, more particularly when it is due to resistant or multi-resistant bacteria.

Drug-resistant bacteria and/or fungus and/or viruses appear more and more frequently, in particular in hospitals, where they may lead to nosocomial infections, which may cause nosocomial syndrom. Thus fighting against this bacteria and/or fungus and/or viruses allows preventing and/or treating at least some nosocomial infections.

The pharmaceutical composition may also be used for treatment and/or prevention of syndromes met in the following etiology:

infections passing through intact epithelial barrier, such as infections by inhalation or by ingestion;

infections passing through discontinuous epithelial barrier, such as infections by biting, cuttings, wounds, injection, transplantation, transfusion;

infections linked to the use of an invasive medical device, such as a prosthesis or a stent;

surgery, peri-surgery and post surgery infections;

infections resulting from burns.

The pharmaceutical composition may also be used for treating and/or preventing the travel of bacteria, in particular such as Staphyllococcus *aureus*, in the different flora of the subject, in particular cutaneous flora, buccal flora and nose-throat flora.

The composition may be intended to be applied on skin and/or mucosa, on a device intended to contact skin and/or mucosa, and/or on a device intended to break the epidermal barrier.

Following one aspect, the invention has for subject matter a process for prophylaxis or for preventing microbial, such as bacterial and/or fungal and/or viral infections, in particular nosocomial, comprising the step of applying the composition, in particular the pharmaceutical composition, on the skin or on the mucosa surface where the epithelium barrier is or risks to be broken or damaged, such as by the use of a catheter, or presenting a break allowing the passage of microbes, such as bacteria and/or fungus.

The composition, especially the pharmaceutical composition, may be formulated for topic or systemic administration, per os or parenteral administration. In particular, for:

injection administration, such as pulmonary, intravenous, subcutaneous intramuscular and/or intraperitoneal formulation; the composition may thus be hydrophobic or hydrophilic.

local administration (rectal, cutaneous), oral administration.

The composition may be presented as a liquid, a paste, a powder, a pomade, an emulsion, a cream, a gel, a tablet, a gelule.

The composition may be under hydrophobic form, meaning being free of water and or polar solvent.

When under the gel form, the viscosity may go from 500 to 2 000, in particular from 750 to 1 500 centipoise (cP). It may be measured at 25° C. with a CPE52 rotor at 250 rpm.

The composition, in particular as a pomade, a gel or a cream, may comprise polyethylène glycol, in particular macrogol 400, medium chains triglycerides and/or *soja* oil.

The composition, may also comprise colloidal silica.

When under an emulsion form, the composition may comprise a gelling agent, which may be a polymer, such as polyvinyl pyrrolidone, in particular povidone, for example povidone K30®.

The emulsion may comprise a surfactant, for example such as a polysorbate, polyglyceryl oleate or capric/caprylic acids glycerides.

A hydrophilic composition may comprise a gelling agent and/or a surfactant, in particular such as disclosed above.

The intravenous formulation may comprise polyvinylpyrrolidone.

Following an embodiment, the composition, in particular pharmaceutical, comprises a large spectrum antiseptic, such as chlorhexidine, chlorine or iodine, in particular polyvidone iodine, such as betadine.

Following another embodiment, the invention has for subject matter a patch comprising a composition, in particular a pharmaceutical composition, according to the invention.

According to still another aspect, the invention has for subject matter a treatment of microbial infection, in particular such as disclosed above, in which an efficient amount of active blend is delivered to a subject. The medicament can be administered at a dosage regime of one, two or three times per day. The dose can be determined by the doctor on the basis of his general knowledge. Initial PK/PD models in healthy CD-1 and Balb/c mice of both sexes suggested a maximal tolerated dose of 300 mg/kg with no clinically relevant adverse effect and no major biochemical and haematological change after 15×100 mg doses. Preliminary kinetic data suggest a rapid elimination of the active blends of the invention in particular active blend 9, with a remaining MRSA inhibition by plasma during 2 hours, in line with bibliographic data on the main compound, cinnamaldehyde (1.7 h).

In a further object of the invention, the composition is used as a cleaning agent, in particular to clean medical devices which are intended to be in contact with the skin or mucosa, and more particularly when potential breaches may exist. For example this composition may be used on skin surface where an infusion is to be done or on skin or mucosa surface where a catheter is used, in particular urinary catheter.

In a further object of the invention, the composition is used as a cleaning or protecting agent, in particular against microbially induced corrosion.

The composition may also be used as a conservative, in particular for food or cosmetic composition.

The composition may also be used for cleaning and/or protecting a surface from a secondary colonisation The following examples are intended to illustrate the invention and in no way to limit it.

EXAMPLES

Example 1: Bacterial Strains

The tested strains have been isolated from various samplings from human patients (blood, urines, pulmonary aspiration, etc). They have been isolated from patients non-infected at their admission to the hospital and who have developed an infection after at least 48 h of hospitalisation. The studied strains are as follows:

Example 2: Antibacterial Activity of Blend 1

Following a method allowing the dissolution of the active blend in a Mueller Hinton gelose the following MIC has been measured with the following active blend 1 consisting of 1% by weight of cineole, 2.4% by weight of linalool, 1.7% by weight of beta-caryophyllene, 86.7% by weight of trans-cinnamaldehyde, 5.35% by weight of trans-2-methoxycinnamaldehyde, 0.35% by weight of benzyl benzoate, and 2.5% by weight of cinnamyl acetate compared to the total weight of the active blend. Said active blend 1 having been tested at concentrations shown in the following table.

TABLE 2

| Strain | Type | MIC (% v/v) | Strain | Type | MIC (% v/v) |
|---|---|---|---|---|---|
| ATCC 25922 | *E. coli* | 0.03 | 8241 | *Staphylococcus* | 0.03 |
| 8127 | *Pseudomonas* | 0.125 | 8152 | *Enterococcus* | 0.03 |

TABLE 1

| *Enterobacteriaceae* | n = 89 |
|---|---|
| *Citrobacter freundii* | Phenotypic characterisation: Cephalosporinase, WSBL, Wild<br>Genotypic characterisation: CTX M1, CTX M15, KPC-2, NDM-1, TEM 3 |
| *Enterobacter cloacae* | Phenotypic characterisation: Cephalosporinase (HN2), WSBL, Wild<br>Genotypic characterisation: GES–, KPC-2, NDM-1, NMC-A, OXA-43 |
| *Escherichia coli* | Phenotypic characterisation: WSBL, Wild, Penicilinases, Fluoroquinolone resistance, Nalixidic acid resistance<br>Genotypic characterisation: CMY.2, CTX M1, CTX M14, CTX M15, CTX M3, KPC-2, NDM-1, OXA-30, OXA-48, SHV-12, SHV-2A, TEM-12, VIM-1, VIM-19, VIM-2 |
| *Klebsiella pneumoniae* | Phenotypic characterisation: Penicillinase, wild<br>Genotypic characterisation: OXA-48; ACT-1, CTX M14, CTX M15, CTX M2, CTX M3, DHA-2, KPC-2, KPC-3, LAT-1, NDM-1, SHV, SHV-12, SHV-2A, TEM-2, TEM-3, VIM |
| *Proteus mirabilis* | Phenotypic characterisation: penicillinase, wild<br>Genotypic characterisation: ACC 1, TEM-21, TEM-52 |
| *Salmonella* sp | Phenotypic characterisation: wild<br>Genotypic characterisation: CMY 2 |
| *Serratia marscescens* | Phenotypic characterisation: Cephalosporinase (HN 1 and 2), wild<br>Genotypic characterisation: KPC-2, SME-1, SME-2 |
| *Providencia stuartii* | Phenotypic characterisation: wild<br>Genotypic characterisation |
| Other Gram - *Bacilli* | n = 20 |
| *Acinetobacter baumanii* | Phenotypic characterisation: multiresistant<br>Genotypic characterisation: VEB-1, VIM-4 |
| *Burkholderia cepacia* | Phenotypic characterisation: wild |
| *Pseudomonas aeruginosa* | Genotypic characterisation: WSBL, Cephalosporinase, Penicillinase, Lack of porins, Multiresistant, wild<br>Phenotypic characterisation: VIM-2, GES-2, PER-1 |
| *Staphylococcaceae* | n = 11 |
| *Staphylococcus* | Phenotypic characterisation: Methicillin resistance, fluoroquinolone resistance, Kanamicin resistance, Tobramicin resistance, multiresistance, Wild<br>Genotypic characterisation: None |
| *Streptococcus* et app | n = 4 |
| *Enterococcus* sp | Phenotypic characterisation: Erythromicin, clyndamicin, pristinamicin, Wild<br>Genotypic characterisation: none |

TABLE 2-continued

| Strain | Type | MIC (% v/v) | Strain | Type | MIC (% v/v) |
|---|---|---|---|---|---|
| 8128 | Pseudomonas | 0.125 | 8153 | Enterococcus | 0.03 |
| 8129 | Pseudomonas | 0.125 | 9001 | E. faecium | 0.03 |
| 8130 | Pseudomonas | 0.125 | 9002 | E. faecium | 0.03 |
| 8131 | Pseudomonas | 0.03 | 9003 | E. coli | 0.03 |
| 8132 | Pseudomonas | 0.125 | 9004 | E. aerogenes | 0.03 |
| 8133 | Pseudomonas | 0.125 | 9007 | P. aeruginosa | 0.06 |
| 8134 | Pseudomonas | 0.125 | 9008 | P. aeruginosa | 0.125 |
| 8135 | Pseudomonas | 0.125 | 9010 | A baumanii | 0.03 |
| 8136 | Pseudomonas | 0.125 | 9011 | A baumanii | 0.03 |
| 8137 | E. coli | 0.03 | ATCC | P. aeruginosa | 0.125 |
| 8138 | E. coli | 0.03 | 10168 | SARM | 0.03 |
| 8141 | E. coli | 0.03 | 10267 | S marcescens | 0.03 |
| 8142 | E. coli | 0.03 | 10268 | C freundii | 0.03 |
| 8150 | E. coli | 0.03 | 10269 | E. coli | 0.03 |
| 8151 | E. coli | 0.03 | 10270 | K pneumoniae | 0.06 |
| 8154 | E. coli | 0.03 | 10271 | S marcescens | 0.03 |
| 8155 | E. coli | 0.03 | 10272 | K pneumoniae | 0.06 |
| 8156 | E. coli | 0.03 | 10273 | E. coli | 0.03 |
| 8157 | E. coli | 0.03 | 10274 | E. cloacae | 0.03 |
| 8143 | Staphylococcus | 0.03 | 10275 | A baumanii | 0.015 |
| 8146 | Staphylococcus | 0.03 | 10276 | PS aeruginosa | 0.06 |
| 8147 | Staphylococcus | 0.03 | 10277 | K pneumoniae | 0.06 |
| 8148 | Staphylococcus | 0.03 | 10278 | P. aeruginosa | 0.06 |
| 8149 | Staphylococcus | 0.03 | 10279 | S marcescens | 0.06 |
| 8237 | Staphylococcus | 0.03 | 10280 | P. aeruginosa | 0.125 |
| 8238 | Staphylococcus | 0.03 | 10281 | E. cloacae | 0.03 |
| 8239 | Staphylococcus | 0.03 | 10282 | B cepacia | 0.03 |
| 8240 | Staphylococcus | 0.03 | 10286 | Candida albicans | 0.00375 |
| ATCC25285 | B. fragilis | 0.001 | 09262 | Bacteroides gpe frag. | 0.001 |
| ATCC29741 | B. thetaiota | 0.001 | 09265 | Bacteroides gpe frag. | 0.001 |
| ATCC43055 | E. lenta | 0.001 | 09266 | Peptostreptococcus spp | 0.002 |
| ATCC700057 | C.difficile | 0.001 | 09267 | B. fragilis | 0.001 |
| 09022 | C. difficile | 0.002 | 09269 | Bacteroides gpe frag. | 0.001 |
| 09027 | C. difficile | 0.001 | 09273 | C clostridioforme | 0.001 |
| 09028 | C. difficile | 0.002 | 09275 | B. vulgaris | 0.001 |
| 09038 | C. difficile | 0.001 | 09277 | Bacteroides gpe frag. | 0.001 |
| 09198 | C clostridioforme | 0.001 | 09279 | B. fragilis | 0.001 |
| 09252 | B. fragilis | 0.001 | 09280 | Bacteroides gpe frag. | 0.001 |
| 09253 | Peptostreptococcus spp | 0.001 | 09282 | Peptostreptococcus spp | 0.001 |
| 09254 | Micromonas m. | 0.001 | 09284 | Bacteroides gpe frag. | 0.001 |
| 09255 | Bacteroides gpe frag. | 0.001 | 09296 | B. fragilis | 0.001 |
| 09256 | Micromonas m. | 0.001 | 09297 | B. fragilis | 0.001 |
| 09257 | Peptostreptococcus spp | 0.001 | 09298 | B. fragilis | 0.001 |
| 09259 | C. perfrinfgens | 0.002 | 09299 | C. difficile | 0.001 |
| 09260 | B. vulgaris | 0.001 | 09304 | Bacteroides gpe frag. | 0.001 |
| 09261 | Peptostreptococcus spp | 0.001 | 09305 | Bacteroides gpe frag. | 0.001 |

Antibacterial activity appears to be quite constant on every strain, regardless to the type of cell wall structure and to the presence of antibiotic resistance. One will note, with big interest, that active blend 9 is also active against anaerobic bacteria.

Example 3: Antibacterial Activity of Active Blends 2, 3, 4 and 5

Following a method allowing the dissolution of the active blend in a Mueller Hinton gelose the following MIC has been measured with the following active blends:

Active blend 2 consisting of 2.4% by weight of linalool, 1.72% by weight of beta-caryophyllene, 87.58% by weight of trans-cinnamaldehyde, 5.43% by weight of trans-2-methoxycinnamaldehyde, 0.34% by weight of benzyl benzoate, and 2.53% by weight of cinnamyl acetate compared to the total weight of the active blend, and Active blend 3 consisting of 1.04% by weight of cineole, 2.42% by weight of linalool, 88.19% by weight of trans-cinnamaldehyde, 5.47% by weight of trans-2-methoxycinnamaldehyde, 0.35% by weight of benzyl benzoate, and 2.54% by weight of cinnamyl acetate compared to the total weight of the active blend, active blend 4 consisting of 2.41% by weight of linalool, 1.72% by weight of beta-caryophyllene, 87.88% by weight of trans-cinnamaldehyde, 5.45% by weight of trans-2-methoxycinnamaldehyde, and 2.53% by weight of cinnamyl acetate compared to the total weight of the active blend;

active blend 5 consisting of 1.02% by weight of cineole, 2.39% by weight of linalool, 1.71% by weight of beta-caryophyllene, 86.98% by weight of trans-cinnamaldehyde, 5.39% by weight of trans-2-methoxycinnamaldehyde, and 2.51% by weight of cinnamyl acetate compared to the total weight of the active blend.

The MICs (%) of active blends 1, 2, 3 and 4 are shown in the following table.

TABLE 3

| Name | Reference | Active blend 2 | Active blend 3 | Active blend 4 | Active blend 5 | Active blend 1 |
|---|---|---|---|---|---|---|
| E. coli | ATCC 25922 | 0.03 | 0.03 | 0 | 0.03 | 0.015 |
| Pseudomonas | 8127 | 0.125 | 0.125 | 0.125 | 0.125 | 0.060 |
| Pseudomonas | 8128 | 0.125 | 0.125 | 0.125 | 0.125 | 0.060 |
| Pseudomonas | 8129* | 0.125 | 0.03 | 0.125 | 0.03 | 0.060 |
| Pseudomonas | 8130* | 0.125 | 0.125 | 0.125 | 0.125 | 0.125 |
| Pseudomonas | 8131* | 0.125 | 0.125 | 0.125 | 0.125 | 0.060 |
| Pseudomonas | 8132* | 0.125 | 0.06 | 0.125 | 0.125 | 0.125 |
| Pseudomonas | 8133 | 0.125 | 0.06 | 0.125 | 0.06 | 0.060 |
| Pseudomonas | 8134 | 0.125 | 0.06 | 0.125 | 0.06 | 0.125 |
| Pseudomonas | 8135* | 0.125 | 0.06 | 0.125 | 0.125 | 0.015 |
| Pseudomonas | 8136* | 0.125 | 0.125 | 0.125 | 0.125 | 0.015 |
| E. coli | 8137 | 0.03 | 0.03 | 0.03 | 0.03 | 0.015 |
| E. coli | 8138 | 0.03 | 0.03 | 0.03 | 0.03 | 0.030 |
| E. coli | 8141 | 0.06 | 0.03 | 0.06 | 0.03 | 0.030 |
| E. coli | 8142 | 0.03 | 0.03 | 0.03 | 0.03 | 0.015 |
| E. coli | 8150 | 0.03 | 0.03 | 0.03 | 0.03 | 0.030 |
| E. coli | 8151 | 0.03 | 0.03 | 0.03 | 0.03 | 0.030 |
| E. coli | 8154 | 0.03 | 0.03 | 0.03 | 0.03 | 0.030 |
| E. coli | 8155 | 0.03 | 0.03 | 0.03 | 0.03 | 0.015 |

TABLE 3-continued

| Name | Reference | Active blend 2 | Active blend 3 | Active blend 4 | Active blend 5 | Active blend 1 |
|---|---|---|---|---|---|---|
| E. coli | 8156 | 0.03 | 0.03 | 0.03 | 0.03 | 0.015 |
| E. coli | 8157 | 0.03 | 0.03 | 0.03 | 0.03 | 0.015 |
| Staphylococcus | 8143 | 0.03 | 0.03 | 0.03 | 0.03 | 0.015 |
| Staphylococcus | 8146 | 0.03 | 0.03 | 0.03 | 0.03 | 0.015 |
| Staphylococcus | 8147 | 0.03 | 0.03 | 0.03 | 0.03 | 0.015 |
| Staphylococcus | 8148 | 0.06 | 0.03 | 0.03 | 0.03 | 0.030 |
| Staphylococcus | 8149 | 0.03 | 0.03 | 0.03 | 0.03 | 0.015 |
| Staphylococcus | 8237 | 0.015 | 0.03 | 0.03 | 0.00375 | 0.015 |
| Staphylococcus | 8238 | 0.03 | 0.03 | 0.03 | 0.03 | 0.030 |
| Staphylococcus | 8239 | 0.06 | 0.03 | 0.03 | 0.03 | 0.030 |
| Staphylococcus | 8240 | 0.06 | 0.03 | 0.03 | 0.03 | 0.030 |
| Staphylococcus | 8241 | 0.06 | 0.03 | 0.03 | 0.03 | 0.030 |
| Enterococcus | 8152 | 0.06 | 0.03 | 0.06 | 0.03 | 0.030 |
| Enterococcus | 8153 | 0.06 | 0.03 | 0.06 | 0.03 | 0.030 |
| Enterococcus faecium | 09001 | 0.03 | 0.015 | 0.06 | 0.125 | 0.015 |
| Enterococcus faecium | 09002 | 0.03 | 0.015 | 0.06 | 0.03 | 0.015 |
| E .coli | 09003 | 0.06 | 0.015 | 0.06 | 0.03 | 0.030 |
| Enterobacter aerogenes | 09004 | 0.06 | 0.015 | 0.06 | 0.03 | 0.030 |
| PS aeruginosa | 09007 | 0.125 | 0.06 | 0.125 | 0.03 | 0.015 |
| Ps aeruginosa | 09008 | 0.125 | 0.125 | 0.125 | 0.06 | 0.015 |
| A baumanii | 09010 | 0.0075 | 0.015 | 0.03 | 0.125 | 0.030 |
| A baumanii | 09011 | 0.0075 | 0.015 | 0.03 | 0.03 | 0.015 |

Antibacterial activity appears to be quite constant on every strain, regardless to the type of cell wall structure and to the presence of antibiotic resistance.

Example 4: Efficacy of Active Blend 1

Active blend 1 was thus tested against 123 strains isolated from nosocomial representing the main resistances mechanisms).

TABLE 4

| Genus | n | CMI 50 | CMI 90 | range |
|---|---|---|---|---|
| Enterobacteriaceae | | | | |
| Citrobacter freundii | 7 | 300 | 300 | 300 |
| Enterobacter aerogenes | 1 | 300 | 300 | 300 |
| Enterobacter cloacae | 8 | 300 | 300 | 300 |
| Escherichia coli | 30 | 300 | 300 | 150-300 |
| Klebsiella oxytoca | 3 | 300 | 300 | 300 |
| Klebsiella pneumoniae | 20 | 300 | 600 | 300-600 |
| Proteus mirabilis | 6 | 300 | 300 | 300 |
| Providencia stuartii | 2 | 300 | 300 | 300 |
| Salmonella sp | 5 | 300 | 300 | 300 |
| Serratia marcescens | 6 | 600 | 600 | 300-600 |
| Other gram - Bacilli | | | | |
| Acinetobacter baumannii | 3 | 150 | 300 | 150-300 |
| Burkholderia cepacia | 1 | 75 | 75 | 75 |
| Pseudomonas aeruginosa | 16 | 600 | 600 | 600-1250 |
| Staphylococcaceae | | | | |
| Staphylococcus aureus | 11 | 300 | 300 | 300 |
| Enterococcus & rel. strains | | | | |
| Enterococcus faecium | 2 | 600 | 300 | 300-600 |
| Enterococcus sp | 2 | 300 | 300 | 300 |

These results confirm the wide-spectrum efficiency of active blend 1 as the blend is active against all strains tested. MIC levels are quite constant and differences within one genus are never higher than one dilution.

While most genera have an in vitro MIC of 300 mg/L, some are especially susceptible (Acinetobacter and Burkholderia) while some others are little less susceptible (Serratia, Pseudomonas and Enterococcus).

Example 5: Bactericidal Activity of Blend 1

Bacteria Numbering

The numberings are done by successive dilutions of tenth of the samples. Each dilution (100 µl) is spread on a Mueller Hinton gelose. The numbering is done on a Petri dish which contains between 15 and 150 colonies. The numbering threshold is thus 150 UFC/ml.

Neutralising Power of D/E

To stop the activity of the active blend after a defined time, 100 µl of the mixture active blend+ bacteria is taken and diluted in 900 µl of a neutraliser dilutant in order to block the anti-bacterial action of the active blend.

The used neutraliser is the «Neutralizing broth for neutralizing and testing disinfectants and antiseptics» from Dey and Engley marketed by Criterion, with the following formula:

Glucose (10 g), lecithine (7 g), caseine peptone (5 g), Tween 80 (5 g), sodium thiosulfate (6 g), bipotassic phosphate (3.3 g), sodium bisulfate (2.5 g), yeast extract (2.5 g sodium), thioglycollate (1 g), monopotassic phosphate (0.1 g) and bromocresol purple (20 mg). The obtained powder is dissolved in a litre of deionised water, and the, after heating and dissolution, the medium is sterilised by going in an oven at 121° C. for 15 minutes. The final pH is 7.6±0.2.

A neutraliser control is done as follows:

A mixture active blend+neutraliser (half and half) is contacted with the bacterial inoculum. After 48 h à 37° C. of incubation, bacterial numbering should not be less than 50% of the control numbering. This allows demonstrating the absence of activity of the neutraliser and in particular the fact that the neutraliser blocks completely the anti-bacterial action of the active blend, avoiding the carry over phenomenon.

Bactericidal Activity Measure of the Active Blends

After 15, 30, 45 and 60 minutes of contacting active blend+bacteria, 100 µl of the mixture product/bacteria is taken and added to 900 µl neutraliser, then two dilution ($10^{th}$ and $100^{th}$) are done with cysteinated Ringer. The, 100 µl of each of the dilution is spread on a Mueller Hinton gelose. The dishes are then incubated 48 h and survivors are numbered.

The dose of active blend is corresponding to MIC×4 of each of the tested strain.

Results Expression

By definition bactericidal effect is obtained if a minimum fall of 3 logarithms is observed from the starting inoculum. A graph of the bactericidy linking the bacteria number with the contact time with the active blend may be drawn; this allows to check if the bactericidy is intense and fast or slow.

Results:

For example, the active blend 1 shows a bactericidy on the 8132, 8239, 8154, 9004 strains. The results are shown in the following tables.

TABLE 5

Strain 8132 and Strain 8239

| | Strain 8132 | | Strain 8239 | |
|---|---|---|---|---|
| Log CFU/ml | Control | Active blend 9 (MIC × 4) | Control | Active blend 9 (MIC × 4) |
| T0 | 8.00E+05 | 8.10E+05 | 3.20E+05 | 4.00E+05 |
| T15 | 5.50E+05 | 2.00E+02 | 2.90E+05 | 2.00E+04 |

TABLE 5-continued

Strain 8132 and Strain 8239

| | Strain 8132 | | Strain 8239 | |
|---|---|---|---|---|
| Log CFU/ml | Control | Active blend 9 (MIC × 4) | Control | Active blend 9 (MIC × 4) |
| T30 | 4.70E+05 | 1.00E+02 | 4.10E+05 | 2.00E+03 |
| T45 | 4.40E+05 | 1.00E+02 | 3.10E+05 | 1.00E+03 |
| T60 | 5.50E+05 | 1.00E+02 | 2.50E+05 | 00E+02 |

TABLE 6

Strain 8154 and Strain 9004

| | Strain 8154 | | Strain 9004 | |
|---|---|---|---|---|
| Log CFU/ml | control | Active blend 9 (MIC × 4) | Control | Active blend 9 (MIC × 4) |
| T0 | 4.70E+06 | 4.60E+06 | 1.12E+07 | 8.90E+05 |
| T15 | 4.60E+06 | 1.00E+01 | 1.06E+07 | 1.00E+02 |
| T30 | 4.00E+06 | 1.00E+01 | 1.09E+07 | 1.00E+02 |
| T45 | 3.30E+06 | 1.00E+01 | 1.03E+07 | 1.00E+02 |
| T60 | 2.50E+06 | 1.00E+01 | 1.01E+07 | 1.00E+02 |

Bactericidal effect of active blend 1 was then analyzed with killing-curves for 60 strains at 4× the MIC, and compared to CNM at 4× the MIC and active blend 9 at 1% (positive control). Results are expressed in minutes necessary to reduce bacterial counts by 1 log.

TABLE 7

| | Mean Log reduction time (min) | | |
|---|---|---|---|
| | Active blend 1 (1%) | Active blend 1 (MIC × 4) | CNM (MIC × 4) |
| Enterobacteria | 6 | 40 | 72 |
| Other gram - | 6 | 23 | 95 |
| Cocci G+ | 49 | 126 | 195 |
| All strains | 19 | 51 | 111 |

* $p < 0.05$ vs. CNM, NS not significative (student test)

Active blend 1 showed a mean lag of 50.8 minutes at 4×MIC and 15.6 minutes at 1% (Table 7). For seven strains, reduction of count was not observed at 4× the MIC of active blend 1 but active blend 1 was bactericidal for all strains at 1%.

Example 6: Kinetics STUDIES

Growing capacities of 4 bacteria (NDM-1 E. coli, Multiresistant Enterococcus sp, VIM-2 P. aeruginosa and OXA-48 K. pneumoniae) in contact with active blend 1 was tested at three different concentrations: MIC, MIC/2, MIC/4, MIC/8 and MIC/16.

The results are reported in FIGS. 2 to 6.

Active blend 1 shows a bactericidal effect at MIC on K. pneumonia only while the other strains present a stable count of bacteria at MIC. Surprisingly, for the four strains, count of bacteria are stable during 12 hours at MIC/2 and 4 hours at MIC/4, indicating that active blend 1 is able to decrease bacterial division capabilities at sub-MIC concentrations.

Example 7: Internal Synergy

Following a method allowing the dissolution of the active blend in a Mueller Hinton gelose the MIC has been measured with pure components of the active blend 1.

TABLE 8

| Product CAS number (chemical class) | Values | Staphylococcus And Enterococcus n = 14 | Enterobacteriaceae n = 13 | Other Gram - rods n = 15 |
|---|---|---|---|---|
| Cinnamaldehyde 1431-10-9 (P) | MIC 50 | 150 | 150 | 600 |
| | MIC 90 | 300 | 600 | 1250 |
| | Range | 150-300 | 150-600 | 150-1250 |
| Trans-methoxy-cinnamaldehyde 1504-74 | Range | >10000 | >10000 | >10000 |
| Cinnamyl acetate 103-54-8 (P) | MIC 50 | >10000 | >10000 | >10000 |
| | MIC 90 | >10000 | >10000 | >10000 |
| | Range | 5000-10000 | >10000 | 2500->10000 |
| Linalool 78-70-6 (T) | MIC 50 | 2500 | 2500 | >10000 |
| | MIC 90 | 10000 | 10000 | >10000 |
| | Range | 2500-10000 | 2500->10000 | 2500->10000 |
| Caryophyllene 87-44-5 (T) | MIC 50 | >10000 | >10000 | >10000 |
| | MIC 90 | >10000 | >10000 | >10000 |
| | Range | 1250->10000 | >10000 | >10000 |
| Cineole 470-82-6 (T) | Range | >10000 | >10000 | >10000 |
| Benzyl benzoate 120-51-4 (P) | Range | >10000 | >10000 | >10000 |

Table 8 shows that only cinnamaldehyde (CNM) is highly effective on all the strains. 3 compounds present no activity at the tested concentrations. The other compounds show specific activities with either narrow, intermediate or wide spectrum for caryophyllen, cinnamaldehyde acetate (CNM-A) and linalool respectively.

In table 9, the results for active blends 2 to 4/blends 5 to 9 are compared to active blend 1 (the most active) and are expressed in terms of dilution (value=Log 2 (CMI active blend or component/CMI active blend 1)).

TABLE 9

| Name | Reference | M2 | M3 | M4 | M5 | M6 | M7 | M8 | M9 | M1 |
|---|---|---|---|---|---|---|---|---|---|---|
| E. coli | ATCC 25922 | 1.0 | 1.0 | NA | 1.0 | 1.0 | 1.0 | 1.0 | 1.0 | 0.0 |
| Pseudomonas | 8127 | 1.1 | 1.1 | 1.1 | 1.1 | 1.1 | 1.1 | 1.1 | 1.1 | 0.0 |
| Pseudomonas | 8128 | 1.1 | 1.1 | 1.1 | 1.1 | 1.1 | 1.1 | 1.1 | 1.1 | 0.0 |
| Pseudomonas | 8129* | 1.1 | −1.0 | 1.1 | 0.0 | 0.0 | −1.0 | 1.1 | 1.1 | 0.0 |
| Pseudomonas | 8130* | 0.0 | 0.0 | 0.0 | 0.0 | 0.0 | 0.0 | 0.0 | 0.0 | 0.0 |
| Pseudomonas | 8131* | 1.1 | 1.1 | 1.1 | 1.1 | 1.1 | 1.1 | 1.1 | 1.1 | 0.0 |
| Pseudomonas | 8132* | 0.0 | −1.1 | 0.0 | 0.0 | 0.0 | 0.0 | 0.0 | 0.0 | 0.0 |
| Pseudomonas | 8133 | 1.1 | 0.0 | 1.1 | 0.0 | −1.0 | 0.0 | 0.0 | 0.0 | 0.0 |
| Pseudomonas | 8134 | 0.0 | −1.1 | 0.0 | −1.1 | −2.1 | −1.1 | −1.1 | 0.0 | 0.0 |
| Pseudomonas | 8135* | 3.1 | 2.0 | 3.1 | 3.1 | 3.1 | 3.1 | 3.1 | 3.1 | 0.0 |
| Pseudomonas | 8136* | 3.1 | 3.1 | 3.1 | 3.1 | 3.1 | 3.1 | 3.1 | 3.1 | 0.0 |
| E. coli | 8137 | 1.0 | 1.0 | 1.0 | 1.0 | 1.0 | 1.0 | 1.0 | 1.0 | 0.0 |
| E. coli | 8138 | 0.0 | 0.0 | 0.0 | 0.0 | 0.0 | 0.0 | 0.0 | 0.0 | 0.0 |
| E. coli | 8141 | 1.0 | 0.0 | 1.0 | 0.0 | 0.0 | 0.0 | 0.0 | 0.0 | 0.0 |
| E. coli | 8142 | 1.0 | 1.0 | 1.0 | 1.0 | 1.0 | 1.0 | 1.0 | 1.0 | 0.0 |
| E. coli | 8150 | 0.0 | 0.0 | 0.0 | 0.0 | 0.0 | 0.0 | 0.0 | 0.0 | 0.0 |
| E. coli | 8151 | 0.0 | 0.0 | 0.0 | 0.0 | 0.0 | 0.0 | 0.0 | 0.0 | 0.0 |
| E. coli | 8154 | 0.0 | 0.0 | 0.0 | 0.0 | 0.0 | 0.0 | 0.0 | 0.0 | 0.0 |
| E. coli | 8155 | 1.0 | 1.0 | 1.0 | 1.0 | 1.0 | 1.0 | 1.0 | 1.0 | 0.0 |
| E. coli | 8156 | 1.0 | 1.0 | 1.0 | 1.0 | 1.0 | 1.0 | 1.0 | 1.0 | 0.0 |
| E. coli | 8157 | 1.0 | 1.0 | 1.0 | 1.0 | 1.0 | 1.0 | 1.0 | 1.0 | 0.0 |
| Staphylococcus | 8143 | 1.0 | 1.0 | 1.0 | 1.0 | 1.0 | 1.0 | 1.0 | 1.0 | 0.0 |
| Staphylococcus | 8146 | 1.0 | 1.0 | 1.0 | 1.0 | 1.0 | 1.0 | 1.0 | 1.0 | 0.0 |
| Staphylococcus | 8147 | 1.0 | 1.0 | 1.0 | 1.0 | 1.0 | 1.0 | 1.0 | 1.0 | 0.0 |
| Staphylococcus | 8148 | 1.0 | 0.0 | 0.0 | 0.0 | 0.0 | 0.0 | 0.0 | 0.0 | 0.0 |
| Staphylococcus | 8149 | 1.0 | 1.0 | 1.0 | 1.0 | 1.0 | 1.0 | 1.0 | 1.0 | 0.0 |
| Staphylococcus | 8237 | 0.0 | 1.0 | 1.0 | 0.0 | NA | NA | NA | 0.0 | 0.0 |
| Staphylococcus | 8238 | 0.0 | 0.0 | 0.0 | 0.0 | 0.0 | 0.0 | 0.0 | 0.0 | 0.0 |
| Staphylococcus | 8239 | 1.0 | 0.0 | 0.0 | 0.0 | 0.0 | 0.0 | 0.0 | 0.0 | 0.0 |
| Staphylococcus | 8240 | 1.0 | 0.0 | 0.0 | 0.0 | 0.0 | 0.0 | 0.0 | 0.0 | 0.0 |
| Staphylococcus | 8241 | 1.0 | 0.0 | 0.0 | 0.0 | 0.0 | 0.0 | 0.0 | 0.0 | 0.0 |
| Enterococcus | 8152 | 1.0 | 0.0 | 1.0 | 1.0 | 0.0 | 0.0 | 1.0 | 0.0 | 0.0 |
| Enterococcus | 8153 | 1.0 | 0.0 | 1.0 | 1.0 | 0.0 | 0.0 | 1.0 | 0.0 | 0.0 |
| PS aeruginosa | ATCC | 1.0 | 3.1 | 3.1 | 1.0 | 3.1 | 3.1 | 3.1 | 3.1 | 0.0 |
| Enterococcus faecium | 09001 | 1.0 | 0.0 | 2.0 | 1.0 | 1.0 | 1.0 | 1.0 | 1.0 | 0.0 |
| Enterococcus faecium | 09002 | 1.0 | 0.0 | 2.0 | 1.0 | 1.0 | 1.0 | 1.0 | 1.0 | 0.0 |
| E .coli | 09003 | 1.0 | −1.0 | 1.0 | 0.0 | 0.0 | 0.0 | 0.0 | 0.0 | 0.0 |
| Enterobacter aerogenes | 09004 | 1.0 | −1.0 | 1.0 | 1.0 | 0.0 | 0.0 | 1.0 | 0.0 | 0.0 |
| PS aeruginosa | 09007 | 3.1 | 2.0 | 3.1 | 2.0 | 3.1 | 2.0 | 3.1 | 3.1 | 0.0 |
| Ps aeruginosa | 09008 | 3.1 | 3.1 | 3.1 | 1.0 | 3.1 | 3.1 | 3.1 | 3.1 | 0.0 |
| A baumanii | 09010 | −2.0 | −1.0 | 0.0 | 0.0 | 0.0 | 0.0 | 0.0 | 0.0 | 0.0 |
| A baumanii | 09011 | −1.0 | 0.0 | 1.0 | 1.0 | 0.0 | 1.0 | 1.0 | 1.0 | 0.0 |

Following the same method, the MIC has been measured with pure trans-cinnamaldehyde (CNM) and the following active blends:

active blends 1 to 4 blend 5: 1.04% cineole, 1.74% beta-caryophyllene, 5.5% trans-2-methoxycinnamaldehyde, 0.35% benzyl benzoate, 2.56% cinnamyl acetate, 88.80% CNM blend 6: 1.08% cineole, 2.51% linalool, 1.8% beta-caryophyllene, 0.36% benzyl benzoate, 2.46% cinnamyl acetate, 91.61% CNM blend 7: 1.02% cineole, 2.39% linalool, 1.71% beta-caryophyllene, 5.39% trans-2-methoxycinnamaldehyde, 2.51% cinnamyl acetate, 86.98% CNM blend 8: 1.05% cineole, 2.44% linalool, 1.74% beta-caryophyllene, 5.51% trans-2-methoxycinnamaldehyde, 0.35% benzyl benzoate, 86.98% CNM blend 9: 2.55% linalool, 1.82% beta-caryophyllene, 2.68% cinnamyl acetate, 92.95% CNM.

TABLE 10

FIC index with reference to active blend 1

| Name | Reference | M2 | M3 | M5 | M6 | M7 | M8 |
|---|---|---|---|---|---|---|---|
| Enterobacter | 9004 | 0.50 | 0.98 | 0.49 | 0.95 | 1.00 | 0.49 |
| Escherichia | 8137 | 0.50 | 0.49 | 0.49 | 0.47 | 0.50 | 0.49 |
| Escherichia | 8138 | 0.99 | 0.98 | 0.98 | 0.95 | 1.00 | 0.98 |
| Escherichia | 8141 | 0.50 | 0.98 | 0.98 | 0.95 | 1.00 | 0.98 |
| Escherichia | 8142 | 0.50 | 0.49 | 0.49 | 0.47 | 0.50 | 0.49 |
| Escherichia | 8150 | 0.99 | 0.98 | 0.98 | 0.95 | 1.00 | 0.98 |
| Escherichia | 8151 | 0.99 | 0.98 | 0.98 | 0.95 | 1.00 | 0.98 |
| Escherichia | 8154 | 0.99 | 0.98 | 0.98 | 0.95 | 1.00 | 0.98 |
| Escherichia | 8155 | 0.50 | 0.49 | 0.49 | 0.47 | 0.50 | 0.49 |
| Escherichia | 8156 | 0.50 | 0.49 | 0.49 | 0.47 | 0.50 | 0.49 |
| Escherichia | 8157 | 0.50 | 0.49 | 0.49 | 0.47 | 0.50 | 0.49 |
| Escherichia | 9003 | 0.99 | 0.98 | 0.98 | 0.95 | 1.00 | 0.98 |
| Escherichia | ATCC 25922 | 0.50 | 0.49 | 0.49 | 0.47 | 0.50 | 0.49 |
| Acinetobacter | 9010 | 0.99 | 0.49 | 0.49 | 0.47 | 0.50 | 0.49 |
| Acinetobacter | 9011 | 1.98 | 0.98 | 0.98 | 1.89 | 1.00 | 0.98 |
| Pseudomonas | 8127 | 0.48 | 0.47 | 0.47 | 0.45 | 0.48 | 0.47 |

TABLE 10-continued

FIC index with reference to active blend 1

| Name | Reference | M2 | M3 | M5 | M6 | M7 | M8 |
|---|---|---|---|---|---|---|---|
| Pseudomonas | 8128 | 0.48 | 0.47 | 0.47 | 0.45 | 0.48 | 0.47 |
| Pseudomonas | 8129 | 0.48 | 0.98 | 0.98 | 0.95 | 1.00 | 0.47 |
| Pseudomonas | 8130 | 0.99 | 0.98 | 0.98 | 0.95 | 1.00 | 0.98 |
| Pseudomonas | 8131 | 0.48 | 0.47 | 0.47 | 0.45 | 0.48 | 0.47 |
| Pseudomonas | 8132 | 0.99 | 2.05 | 0.98 | 0.95 | 1.00 | 0.98 |
| Pseudomonas | 8133 | 0.48 | 0.98 | 0.98 | 0.95 | 1.00 | 0.98 |
| Pseudomonas | 8134 | 0.12 | 0.25 | 0.24 | 0.24 | 0.25 | 0.24 |
| Pseudomonas | 8135 | 0.12 | 0.25 | 0.12 | 0.11 | 0.12 | 0.12 |
| Pseudomonas | 8136 | 0.12 | 0.12 | 0.12 | 0.11 | 0.12 | 0.12 |
| Pseudomonas | 9007 | 0.48 | 0.98 | 0.98 | 0.45 | 1.00 | 0.47 |
| Pseudomonas | 9008 | 0.48 | 0.47 | 1.95 | 0.45 | 0.48 | 0.47 |
| Pseudomonas | ATCC 27583 | 0.48 | 0.47 | 0.47 | 0.45 | 0.48 | 0.47 |
| Staphylococcus | 8143 | 0.99 | 0.98 | 0.98 | 0.95 | 1.00 | 0.98 |
| Staphylococcus | 8146 | 0.99 | 0.98 | 0.98 | 0.95 | 1.00 | 0.98 |
| Staphylococcus | 8147 | 0.99 | 0.98 | 0.98 | 0.95 | 1.00 | 0.98 |
| Staphylococcus | 8148 | 0.50 | 0.98 | 0.98 | 0.95 | 1.00 | 0.98 |
| Staphylococcus | 8149 | 0.99 | 0.98 | 0.98 | 0.95 | 1.00 | 0.98 |
| Staphylococcus | 8237 | 1.98 | 1.97 | 1.95 | NA | NA | NA |
| Staphylococcus | 8238 | 0.99 | 0.98 | 0.98 | 0.95 | 1.00 | 0.98 |
| Staphylococcus | 8239 | 0.50 | 0.98 | 0.98 | 0.95 | 1.00 | 0.98 |
| Staphylococcus | 8240 | 0.50 | 0.98 | 0.98 | 0.95 | 1.00 | 0.98 |
| Staphylococcus | 8241 | 0.50 | 0.98 | 0.98 | 0.95 | 1.00 | 0.98 |
| Enterococcus | 8152 | 0.50 | 0.98 | 0.49 | 0.95 | 1.00 | 0.49 |
| Enterococcus | 8153 | 0.50 | 0.98 | 0.49 | 0.95 | 1.00 | 0.49 |
| Enterococcus | 9001 | 1.98 | 1.97 | 1.95 | 1.89 | 1.99 | 1.95 |
| Enterococcus | 9002 | 1.98 | 1.97 | 1.95 | 1.89 | 1.99 | 1.95 |

These results show that active blend 1 is the more potent blend. This proves that although the non CNM compounds do not present an activity at the tested concentration as such, their presence in the blend potentiate the antibacterial properties of CNM. All the products from active blend 1 formula are involved in the activity of the blend. Indeed, even when compounds removed are inactive against some bacteria, corresponding blends are less effective or present a narrower spectrum than active blend 1. These results confirm the importance of using blends, either for increasing efficacy or for decreasing toxicity. Indeed MIC measured with active blend 1 are, in overall, lower than those of natural compounds.

Example 8: Activity on Viruses of Active Blend 9

The activity of active blend 9 (M9) on VIH has been tested and compared to the activity of AZT.

TABLE 11

|  | concentration | % Survival (lymphoid cells T4) | Dosage P24 (% inhibition vs T+ of the plate) |
|---|---|---|---|
| AZT | 5 mg/ml | 108.7% | 100 |
|  | 0.5 mg/ml | 97.8% | 100 |
|  | 0.1 mg/ml | 86.0% | 99 |
|  | 0.05 mg/ml | 36.0% | 80 |
|  | 0.005 mg/ml | 7.0% | 48 |
|  | 0.0005 mg/ml | 10.0% | 39 |
| M9 | 0.0005 mg/ml | — | 100 |
|  | 0.00005 mg/ml | 12.5% | 66 |
|  | 0.000005 mg/ml | 6.7% | 44 |
|  | 0.0000005 mg/ml | 5.3% | 43 |
|  | 0.00000005 mg/ml | 9.2% | 48 |
|  | 0.000000005 mg/ml | 14.1% | 37 |

One notes a good inhibition of P24 by active blend 9.

Example 9: Antibacterial Gel

The active blend 1 is solubilised in 93 ml of Macrogol 400 (Lutreol 400). Then colloidal silica (6 g) is added.

The mixture is homogenised to obtain a non flowing gel.

This gel may be used for example for preventing bacterial and/or fungal infections, for example in case of use of a catheter.

Said catheter may be covered by said gel and/or the surface susceptible to have an epithelial breach may be covered with said gel.

The ability of destroying bacteria is measured by an inoculation of a strain of MRSA in the cream, and then viable bacteria are measured.

Results are shown in the following table and FIG. 1, wherein the CFU/ml is represented on the y axis and the time (h) on the x axis.

TABLE 12

| Time (h) | 0 | 0.25 | 0.5 | 1 | 2 | 4 | 24 | 48 |
|---|---|---|---|---|---|---|---|---|
| CFU/ml | 8.70E+06 | 2.70E+06 | 5.50E+06 | 7.30E+06 | 1.80E+06 | 4.40E+05 | 1.00E+01 | 1.00E+01 |

The reduction log time is 4 h10.

Such a gel allows thus the decrease of the amount of bacteria.

Example 10: Interfering Substances

This example (in accordance with NF EN 13727 has been performed with the active blend 1.

TABLE 13

| | Without interfering substance | | With interfering substance | |
|---|---|---|---|---|
| Strain | Minimal Bactericidal Concentration (C0) | Logarithmic fall (LogR) at C0 | Logarithmic fall (LogR) at C0 | Minimal bactericidal Concentration (C1) |
| Pseudomonas Aeruginosa (CIP 103407) | 0.75 % | >5.23 | 4.54 | 1.25% |
| Staphylococcus aureus (CIP 483) | 5% | >5.13 | >5.13 | 5% |

Interfering substances tested are a mixture of bovine albumine (3.0 g/l) and sheep erythrocytes (3.0 ml/1).

Example 11: Treatment of Infected Mice

The test is performed on Balb/c mice aged 10 to 12 weeks.

They are infected by intraperitoneal injection of $4.10^7$ *Staphylococcus aureus*, methicilline resistant, in a growing phase or with *E. coli*.

The day after, a daily treatment is done as follows:
Intact: no infection
Placebo: no treatment, and
Active blend 1 at daily treatment of 50 and 100 mg/kg/j (one or two administration(s) per day).

The data are summarised in the following table.

TABLE 14

| | % survival | Mean Time to death | % vs placebo | Total health score | % vs placebo | Initial mean weight | Total weight | % vs placebo | Final score | % vs placebo |
|---|---|---|---|---|---|---|---|---|---|---|
| MRSA CHALLENGE/10 days observation | | | | | | | | | | |
| Intact | 100 | — | — | 1000 | 59.74% | 19.49 | 1492 | 26.98% | 10 | 42.86% |
| Placebo | 33 | 8.17 | — | 626 | 0.00% | 19.73 | 1175 | 0.00% | 7 | 0.00% |
| Active blend 1 100 mg/kg/d | 100 | — | — | 993 | 58.63% | 23.36 | 1583 | 34.72% | 10 | 42.86% |
| Active blend 1 100 mg/kg/bid | 100 | — | — | 900 | 43.77% | 23.36 | 1832 | 55.91% | 9.2 | 31.43% |
| Vancomicin | 100 | — | — | XXXX | XXXXX | 21.46 | 1110 | 0.63% | 10 | 42.86% |
| *E. COLI* CHALLENGE/7 days observation | | | | | | | | | | |
| Intact | 100 | — | — | 900 | 84.43% | 18.43 | 869 | 26.49% | 10 | 84.50% |
| Placebo | 70 | 3.33 | — | 488 | 0.00% | 17.62 | 687 | 0.00% | 5.42 | 0.00% |
| Active blend 1 100 mg/kg/d | 100 | — | — | 644 | 31.97% | 18.38 | 847 | 23.29% | 6 | 10.70% |
| Active blend 1 100 mg/kg/bid | 40 | 3.67 | 10.00% | 360 | 26.23% | 17.84 | −535 | 22.13% | 5.5 | 1.48% |
| Amoxicillin | 100 | — | — | 678 | 38.93% | 17.83 | 849 | 23.58% | 6 | 10.70% |

Survival rates were improved by active blend 1 at 100 mg/kg/j on both strains model. This parameter was enhanced by 7 days follow up of health scores and bodyweights.

Survival time of mice that did not survive the challenge was quite unchanged (MRSA) or slightly increased (*E. coli* at 100 mg/kg/bid). Excess death at maximal dose on *E. coli* suggests toxic effects in moribund mice. Overall table variations shows that for each strain model, two groups receiving intraperitoneal treatment at 100 mg/kg recovered from challenge (health score, sum of bodyweight).

Example 12: Interaction with Antibiotics

Interactions between active blend 1 and existing antibiotics (amikacin, colistine) have been explored.

Synergistic effects were evaluated with fractional inhibitory concentration (FIC) indexes and antibiotic-active blend 1 combinations were classified as synergistic (FIC<0.5) additional (FIC index between 0.5 and 1), indifferent (between 1 and 4) or antagonistic (>4). For each combinations several dose of antibiotic and active blend 1 were tested, leading to extensive evaluation of the combination and the impact of relative ratios. 56 FIC indexes were then calculated for every combination tested. These FIC index are represented in the tables below.

TABLE 15 synergies between active blend 9 and amikacin

| | | FIC index | | | | |
|---|---|---|---|---|---|---|
| Reference | Name | M9 + (Amik CMI) | M9 + (Amik CMI/2) | M9 + (Amik CMI/4) | M9 + (Amik CMI/16) | M9 + (Amik CMI/32) |
| 10268 | *Citrobacter freundii* | 1.0 | 0.5 | 0.8 | 0.3 | 0.3 |
| 9004 | *Enterobacter aerogenes* | 1.0 | 0.8 | 0.8 | 0.6 | 0.6 |
| 10274 | *Enterobacter cloacae* | 1.0 | 0.5 | 0.3 | 0.1 | 0.1 |
| 10281 | *Enterobacter cloacae* | 1.5 | 0.6 | 0.5 | 0.6 | 0.3 |
| 8137 | *E. coli* | 1.0 | 0.5 | 0.3 | 0.3 | 0.6 |
| 8138 | *E. coli* | 1.0 | 0.5 | 0.8 | 0.3 | 0.6 |

TABLE 15-continued synergies between active blend 9 and amikacin

| Reference | Name | FIC index | | | | |
|---|---|---|---|---|---|---|
| | | M9 + (Amik CMI) | M9 + (Amik CMI/2) | M9 + (Amik CMI/4) | M9 + (Amik CMI/16) | M9 + (Amik CMI/32) |
| 8141 | E. coli | 1.0 | 0.5 | 0.8 | 0.6 | 0.6 |
| 8142 | E. coli | 1.0 | 0.5 | 0.8 | 0.6 | 0.6 |
| 8150 | E. coli | 1.1 | 0.6 | 0.8 | 0.6 | 0.6 |
| 8151 | E. coli | 1.0 | 0.5 | 0.4 | 0.2 | 0.3 |
| 8154 | E. coli | 1.0 | 0.5 | 0.3 | 0.2 | 0.6 |
| 8155 | E. coli | 1.0 | 0.6 | 0.8 | 0.3 | 0.6 |
| 8156 | E. coli | 1.0 | 0.5 | 0.3 | 0.2 | 0.6 |
| 8157 | E. coli | 1.1 | 0.5 | 0.8 | 0.6 | 0.6 |
| 9003 | E. coli | 1.0 | 1.0 | 1.3 | 1.1 | 0.6 |
| 10269 | E. coli | 0.5 | 0.3 | 0.5 | 0.3 | 0.5 |
| 10273 | E. coli | 1.0 | 0.6 | 0.8 | 0.6 | 0.6 |
| 10385 | E. coli | 0.3 | 0.1 | 0.0 | 0.1 | 0.3 |
| 10386 | E. coli | 0.5 | 0.3 | 0.5 | 0.5 | 0.5 |
| 11002 | E. coli | 1.0 | 0.5 | 0.3 | 0.3 | 0.6 |
| ATCC 25922 | E. coli | 2.1 | 2.1 | 2.1 | 2.1 | 2.1 |
| 10270 | K. pneumoniae | 1.0 | 0.6 | 0.5 | 0.4 | 0.3 |
| 10272 | K. pneumoniae | 1.1 | 0.8 | 0.5 | 0.4 | 0.6 |
| 10277 | K. pneumoniae | 1.0 | 0.5 | 0.8 | 0.4 | 0.3 |
| 10267 | Serratia marcescens | 0.1 | 0.1 | 0.5 | 0.3 | 0.3 |
| 10271 | Serratia marcescens | 1.1 | 0.6 | 0.5 | 0.4 | 0.6 |
| 10279 | Serratia marcescens | 1.0 | 0.8 | 0.5 | 0.6 | 0.6 |
| 10286 | Candida albicans | 0.3 | 0.1 | 0.5 | 0.3 | 0.3 |
| 9010 | A. Baumanii | 1.5 | 0.8 | 0.8 | 0.6 | 1.1 |
| 9011 | A. Baumanii | 1.3 | 0.8 | 0.5 | 0.4 | 0.6 |
| 10275 | A. Baumanii | 1.3 | 0.6 | 0.5 | 0.3 | 0.6 |
| 10282 | B. cepacia | 1.1 | 0.6 | 0.3 | 0.2 | 0.1 |
| 8127 | PS aeruginosa | 1.5 | 1.0 | 0.7 | 0.4 | 0.5 |
| 8128 | PS aeruginosa | 2.0 | 1.5 | 1.3 | 0.6 | 1.1 |
| 8129 | PS aeruginosa | 1.0 | 0.7 | 0.7 | 0.4 | 0.3 |
| 8130 | PS aeruginosa | 1.2 | 1.5 | 1.3 | 1.1 | 1.1 |
| 8131 | PS aeruginosa | 1.2 | 1.5 | 1.3 | 1.1 | 0.5 |
| 8132 | PS aeruginosa | 1.0 | 1.0 | 0.2 | 1.0 | 1.0 |
| 8133 | PS aeruginosa | 1.5 | 1.5 | 1.3 | 1.1 | 0.6 |
| 8134 | PS aeruginosa | 1.5 | 1.5 | 1.3 | 1.1 | 0.6 |
| 8135 | PS aeruginosa | 1.2 | 1.0 | 0.7 | 0.6 | 0.5 |
| 8136 | PS aeruginosa | 1.0 | 1.0 | 0.7 | 0.6 | 1.1 |
| 9007 | PS aeruginosa | 1.3 | 0.6 | 0.5 | 0.6 | 0.6 |
| 9008 | PS aeruginosa | 2.0 | 1.5 | 0.8 | 1.1 | 1.1 |
| 10276 | PS aeruginosa | 2.0 | 1.5 | 1.3 | 1.1 | 1.1 |
| 10278 | PS aeruginosa | 2.0 | 1.5 | 0.8 | 0.6 | 1.1 |
| 10280 | PS aeruginosa | 2.0 | 1.5 | 1.3 | 1.1 | 1.1 |
| ATCC 27583 | PS aeruginosa | 1.1 | 1.0 | 0.8 | 0.6 | 0.6 |
| 8143 | Staph. aureus | 1.1 | 0.5 | 0.3 | 0.3 | 0.6 |
| 8146 | Staph. aureus | 1.0 | 0.5 | 0.4 | 0.6 | 0.6 |
| 8147 | Staph. aureus | 1.0 | 0.5 | 0.3 | 0.3 | 0.6 |
| 8148 | Staph. aureus | 1.0 | 0.5 | 0.4 | 0.6 | 0.6 |
| 8149 | Staph. aureus | 1.1 | 1.0 | 0.4 | 0.6 | 0.6 |
| 8237 | Staph. aureus | 1.5 | 1.0 | 0.7 | 0.6 | ## |
| 8238 | Staph. aureus | 1.0 | 0.5 | 0.8 | 0.3 | 0.6 |
| 8239 | Staph. aureus | 1.0 | 0.5 | 0.8 | 0.3 | 0.6 |
| 8240 | Staph. aureus | 1.0 | 0.5 | 0.3 | 0.6 | 0.6 |
| 8241 | Staph. aureus | 1.0 | 0.5 | 0.3 | 0.4 | 0.6 |
| 10168 | Staph. aureus | 1.0 | 0.5 | 0.4 | 0.6 | 0.6 |
| 8152 | Enterococcus sp | 1.0 | 0.8 | 0.4 | 0.6 | 0.6 |
| 8153 | Enterococcus sp | 0.5 | 0.3 | 0.1 | 0.5 | 0.5 |
| 9001 | Enterococcus faecium | 1.0 | 0.5 | 0.3 | 0.2 | 0.3 |
| 9002 | Enterococcus faecium | 0.3 | 0.1 | 0.5 | 0.3 | 0.3 |

TABLE 16 synergies between active blend 9 and colistin

| Reference | Name | FIC index | | | |
|---|---|---|---|---|---|
| | | M9 + (Coli CMI/2) | M9 + (Coli CMI/4) | M9 + (Coli CMI/8) | M9 + (Coli CMI/12) |
| 9010 | A baumanii | 0.57 | 0.50 | 0.63 | 2.06 |
| 9011 | A baumanii | 0.53 | 0.38 | 0.63 | 0.56 |
| 10275 | A baumanii | 0.57 | 0.75 | 0.38 | 0.56 |
| 10282 | B cepacia | 4.97 | 2.48 | 4.24 | 4.12 |
| 10268 | C freundii | 0.75 | 1.25 | 1.13 | 1.06 |
| 10274 | E. cloacae | 0.53 | 0.38 | 0.38 | 1.06 |
| 10281 | E. cloacae | 1.00 | 0.75 | 1.13 | 1.06 |
| 8137 | E. coli | 0.52 | 0.28 | 0.38 | 0.31 |
| 8138 | E. coli | 0.52 | 0.32 | 0.38 | 0.56 |
| 8141 | E. coli | 0.52 | 0.28 | 0.38 | 0.56 |
| 8142 | E. coli | 0.52 | 0.27 | 0.25 | 0.31 |
| 8150 | E. coli | 0.75 | 0.50 | 0.38 | 1.06 |
| 8151 | E. coli | 0.51 | 0.28 | 0.25 | 0.31 |
| 8154 | E. coli | 0.52 | 0.28 | 0.38 | 0.31 |
| 8155 | E. coli | 0.53 | 0.50 | 0.63 | 1.06 |
| 8156 | E. coli | 0.53 | 0.32 | 0.38 | 1.06 |
| 8157 | E. coli | 0.63 | 0.50 | 0.63 | 0.31 |
| 9003 | E. coli | 0.53 | 0.38 | 0.38 | 0.56 |
| 10269 | E. coli | 0.53 | 0.32 | 0.63 | 0.56 |
| 10273 | E. coli | 0.57 | 0.50 | 0.63 | 0.56 |
| 10385 | E. coli | 0.53 | 0.38 | 0.63 | 0.56 |
| 10386 | E. coli | 0.75 | 0.50 | 1.13 | 1.06 |
| 11002 | E. coli | 0.57 | 0.38 | 0.38 | 0.56 |
| 11065 | E. coli | 0.51 | 0.27 | 0.19 | 0.19 |
| 11066 | E. coli | 0.51 | 0.38 | 0.63 | 0.31 |
| 11067 | E. coli | 0.51 | 0.38 | 0.63 | 0.31 |
| ATCC 25922 | E. coli | 0.53 | 0.38 | 0.63 | 0.56 |
| 9004 | Enterobacter aerogenes | 0.75 | 0.50 | 1.13 | 1.06 |
| 10270 | K pneumoniae | 0.51 | 0.27 | 0.63 | 0.19 |
| 10272 | K pneumoniae | 0.51 | 0.38 | 0.19 | 0.56 |
| 10277 | K pneumoniae | 0.52 | 0.38 | 0.63 | 0.56 |
| 9007 | PS aeruginosa | 1.00 | 1.25 | 1.13 | 1.06 |
| 9008 | Ps aeruginosa | 0.63 | 1.25 | 1.13 | 2.15 |
| 10276 | PS aeruginosa | 0.75 | 1.25 | 1.13 | 2.15 |
| 10278 | PS aeruginosa | 0.75 | 1.25 | 1.13 | 1.06 |
| 10280 | PS aeruginosa | 0.53 | 0.75 | 1.13 | 1.06 |
| ATCC | PS aeruginosa | 0.52 | 0.50 | 1.13 | 2.15 |
| 8127 | Pseudomonas | 0.50 | 0.37 | 0.37 | 0.54 |
| 8128 | Pseudomonas | 0.51 | 0.75 | 1.13 | 2.15 |
| 8129 | Pseudomonas | 0.53 | 0.73 | 1.13 | 1.06 |
| 8130 | Pseudomonas | 0.51 | 0.31 | 0.61 | 1.06 |
| 8131 | Pseudomonas | 0.50 | 0.49 | 0.61 | 0.54 |
| 8132 | Pseudomonas | 0.52 | 0.49 | 1.13 | 1.06 |
| 8133 | Pseudomonas | 0.56 | 0.75 | 1.13 | 2.15 |
| 8134 | Pseudomonas | 0.51 | 0.75 | 1.13 | 1.06 |
| 8135 | Pseudomonas | 0.51 | 0.49 | 0.61 | 1.06 |
| 8136 | Pseudomonas | 0.62 | 0.73 | 1.13 | 1.06 |
| 10267 | S marcescens | 1.47 | 0.73 | 0.49 | 0.25 |
| 10271 | S marcescens | 1.47 | 0.61 | 0.37 | 0.25 |
| 10279 | S marcescens | 0.98 | 0.49 | 0.28 | 0.25 |
| 8152 | Enterococcus | 2.97 | 2.48 | 2.24 | 2.12 |
| 8153 | Enterococcus | 2.97 | 2.48 | 2.24 | 2.12 |
| 9001 | Enterococcus faecium | 1.97 | 0.98 | 0.74 | 1.12 |
| 9002 | Enterococcus faecium | 1.97 | 1.48 | 1.24 | 1.12 |
| 10168 | SARM | 1.97 | 1.48 | 1.24 | 1.12 |
| 8143 | Staphylococcus | 1.97 | 1.48 | 1.24 | 1.12 |
| 8146 | Staphylococcus | 1.97 | 1.48 | 1.24 | 1.12 |
| 8147 | Staphylococcus | 1.97 | 1.48 | 1.24 | 1.12 |
| 8148 | Staphylococcus | 1.97 | 1.48 | 1.24 | 1.12 |
| 8149 | Staphylococcus | 1.47 | 1.48 | 1.24 | 1.12 |
| 8237 | Staphylococcus | 0.99 | 0.98 | 0.74 | 0.62 |
| 8238 | Staphylococcus | 1.97 | 1.48 | 1.24 | 1.12 |
| 8239 | Staphylococcus | 1.97 | 1.48 | 1.24 | 1.12 |
| 8240 | Staphylococcus | 1.97 | 1.48 | 1.24 | 1.12 |
| 8241 | Staphylococcus | 1.97 | 1.48 | 1.24 | 1.12 |
| 5003 | M smegmatis | 1.47 | 0.98 | 1.24 | 1.12 |
| 10286 | Candida albicans | 1.97 | 0.98 | 0.74 | 1.12 |

Example 13: Formulation for iv

TABLE 17

| iv formulation to be diluted in water | |
|---|---|
| Component | Quantity (% (w/w)) |
| Oil phase | |
| Active blend 9 | 25.00 |
| Aqueous phase | |
| Polysorbate 80 | 3.00 |
| Purified water | 57.00 |
| Povidone (K90D) | 15.00 |

This formulation is thereafter diluted in water.

The invention claimed is:

1. A method for antimicrobial treatment, said method comprising:
   administering to a patient in need thereof a synthetic composition comprising:
   an active blend comprising:
   trans-cinnamaldehyde, trans-2-methoxycinnamaldehyde, cinnamyl acetate, and linalool,
   optionally cineole, beta-caryophyllene, and/or benzyl benzoate,
   wherein the number of compounds in the active blend is equal to or lower than seven,
   optionally a drug,
   wherein the composition is free of coumarin,
   wherein the total amount of safrole is below 1% by weight compared to the total weight of the composition,
   wherein the composition comprises at least one pharmaceutical acceptable excipient, and
   wherein the infection to be treated is a digestive system infection and results from bacteria.

2. The method according to claim 1, wherein the bacteria are drug-resistant bacteria.

3. The method according to claim 1, wherein the bacteria involved in the infection are Gram-negative bacteria.

4. The method according to claim 1 for treating peptic ulcer.

5. A method for antimicrobial treatment, said method comprising:
   administering to a patient in need thereof a synthetic composition comprising:
   an active blend including:
   trans-cinnamaldehyde, trans-2-methoxycinnamaldehyde, cinnamyl acetate, and linalool,
   at least cineole, and/or benzyl benzoate,
   optionally beta-caryophyllene,
   wherein the number of compounds in the active blend is equal to or lower than seven,
   optionally a drug,
   wherein the composition is free of coumarin and safrole,
   wherein the synthetic composition comprises at least one pharmaceutical acceptable excipient, and
   wherein the infection to be treated is a digestive system infection and results from bacteria.

6. The method according to claim 5, wherein the bacteria are drug-resistant bacteria.

* * * * *